(12) United States Patent
Cao

(10) Patent No.: US 7,008,921 B2
(45) Date of Patent: Mar. 7, 2006

(54) MATERIALS AND METHODS RELATING TO ENDOTHELIAL CELL GROWTH INHIBITORS

(75) Inventor: Yihai Cao, Stockholm (SE)

(73) Assignee: Karolinska Innovations AB, Stockholm (SE)

( * ) Notice: Subject to any disclaimer, the term of this patent is extended or adjusted under 35 U.S.C. 154(b) by 411 days.

(21) Appl. No.: 09/946,893

(22) Filed: Sep. 5, 2001

(65) Prior Publication Data

US 2002/0072494 A1   Jun. 13, 2002

Related U.S. Application Data

(60) Provisional application No. 60/230,893, filed on Sep. 5, 2000.

(51) Int. Cl.
*A61K 38/00* (2006.01)
*A61K 49/00* (2006.01)
*C07K 14/00* (2006.01)

(52) U.S. Cl. ............................ 514/2; 530/350; 424/9.2
(58) Field of Classification Search ................ 530/350; 435/69.1; 514/2; 424/9.2
See application file for complete search history.

(56) References Cited

U.S. PATENT DOCUMENTS

| | | | |
|---|---|---|---|
| 4,544,545 A | 10/1985 | Ryan et al. | |
| 5,187,098 A | 2/1993 | Malke et al. | |
| 5,200,340 A | 4/1993 | Foster et al. | |
| 5,637,492 A * | 6/1997 | Dawson et al. | 435/217 |
| 5,639,725 A | 6/1997 | O'Reilly et al. | |
| 5,801,146 A | 9/1998 | Davidson | |
| 5,854,221 A | 12/1998 | Cao et al. | |
| 5,945,403 A * | 8/1999 | Folkman et al. | 514/21 |
| 5,972,896 A | 10/1999 | Davidson | |
| 5,981,484 A | 11/1999 | Davidson | |
| 6,057,122 A | 5/2000 | Davidson | |
| 6,080,728 A | 6/2000 | Mixson | |
| 6,107,473 A | 8/2000 | Albone et al. | |
| 6,200,954 B1 | 3/2001 | Ge et al. | |
| 6,218,517 B1 * | 4/2001 | Suzuki | 530/413 |
| 6,251,867 B1 | 6/2001 | Davidson | |

FOREIGN PATENT DOCUMENTS

| | | |
|---|---|---|
| WO | WO 94/00483 | 1/1994 |
| WO | WO 95/29242 | 11/1995 |
| WO | WO 97/23500 | 7/1997 |
| WO | WO 97/41824 | 11/1997 |
| WO | WO 96/15843 | 4/1998 |
| WO | WO 98/15574 | 4/1998 |
| WO | WO 99/00420 | 6/1998 |
| WO | WO 98/54217 | 12/1998 |
| WO | WO 99/11788 | 3/1999 |
| WO | WO 99/16889 | 4/1999 |
| WO | WO 99/26480 * | 6/1999 |
| WO | WO 99/29861 * | 6/1999 |
| WO | WO 99/32143 | 7/1999 |
| WO | WO 99/35248 | 7/1999 |
| WO | WO 99/39702 | 8/1999 |
| WO | WO 99/51638 | 10/1999 |
| WO | WO 99/61464 | 12/1999 |
| WO | WO 00/03726 | 1/2000 |
| WO | WO 00/04052 | 1/2000 |
| WO | WO 00/06759 | 2/2000 |
| WO | WO 00/10506 | 3/2000 |
| WO | WO 00/61179 | 4/2000 |
| WO | WO 00/31244 | 6/2000 |
| WO | WO 00/47729 A1 * | 8/2000 |
| WO | WO 00/48595 | 8/2000 |
| WO | WO 01/44294 | 6/2001 |

OTHER PUBLICATIONS

Petersen et al. (1990), Characterization of the Gene for Human Plasminogen, a Key Proenzyme in the Fibrinolytic System, J. Biol. Chem. 265(11): 6104-6111.*
Arap et al. (1998), Curr. Opin. Oncol. 10(6): 560-565.*
Rippmann et al. (2000), J. Biochem. 349: 805-812.*
Folkman, J., "Tumor angiogenesis: Therapeutic implications"; N. Engl. Jour. Med., 285: 1182-1186 (1971).
Kim, K.J. et al., "Inhibition of vascular endothelial growth factor-induced angiogenesis suppresses tumor growth in vivo"; Nature, 362: 841-844 (1993).
Hori, A. et al., "Suppression of Solid Tumor Growth by Immunoneutralizing Monoclonal Antibody Against Human Basis Fibroblast Growth Factor"; Cancer Research, 51: 6180-6184 (1991).
Ingber, D. et al., "Anaioinhibins: Synthetic analogues of fumagillin which inhibit angiogenesis and suppress tumour growth"; Nature, 48: 555-557 (1990).

(Continued)

*Primary Examiner*—Janet L. Andres
*Assistant Examiner*—Gyan Chandra
(74) *Attorney, Agent, or Firm*—Dann Dorfman Herrell and Skillman; Kathleen D. Rigaut

(57) ABSTRACT

Proteolytic enzymes are involved in generation of a number of endogenous angiogenesis inhibitors and it has been shown that urokinase-activated plasmin can process plasminogen to release an angiogenesis inhibitor, K1–5 (protease-activated kringles 1–5). However, this proteolytic protein (proteolytic K1–5) cannot be secreted (exported) from cells and thus is limited in its application as a therapeutic. The present inventor has now engineered a recombinant protein derived from plasminogen which is folded correctly such that it can be secreted from cells in which it is expressed. The inventor surprisingly found that in order to fold correctly such that it can be secreted, the recombinant protein must comprise a secretory signal peptide and a pre-activation peptide derived from plasminogen.

25 Claims, 12 Drawing Sheets

OTHER PUBLICATIONS

Arap, W. et al., "Cancer Treatment by Targeted Drug Deliver to Tumor Vasculature in a Mouse Model"; Science, 279: 377-380 (1998).

Jain, R.K. et al., "Quantitative angiogenesis assays: progress and problems"; Nat. Med. 3: 1203-1208 (1997).

Cao, R. et al., "Suppression of angiogenesis and tumor growth by the inhibitor K1-5 generated by plasmin-mediated proteolysis"; Proc. Natl. Acad. Sci. USA, 96: 5728-5733 (1999).

Cao, R. et al., "Interleukin-18 acts as an angiogenesis and tumor suppressor"; FASEB J., 13: 2195-2202 (1999).

Cao, Y. et al., "Angiogenesis inhibited by drinking tea"; Nature, 381: 398 (1999).

Petros, A.M. et al., "Analysis of the aliphatic $^1$H-NMR spectrum of plasminogen kringle 4"; Eur. J. Biochem, 170: 549-563 (1988).

Schaller, J., "Structural Aspects of the Plasminogen of Various Species"; Enzyme, 40: 63-69 (1988).

Ramesh, V. et al., "The aromatic $^1$H-NMR spectrum of plasminogen kringle 4"; Eur. J. Biochem., 159: 581-595 (1986).

Schaller, J. et al., "Complete amino acid sequence of bovine plasminogen"; Eur. J. Biochem., 149: 267-278 (1985).

Cao, Y. et al. "Expression of Angiostatin cDNA in a Murine Fibrosarcoma Suppresses Primary Tumor Growth and Produces Long-Term Dormancy of Metastases"; J. Clin. Invest., 101(5): 1055-1063 (1998).

Cao, Y. "Endogenous Angiogenesis Inhibitors: Angiostatin, Endostatin and Other Proteolytic Fragments"; Progress in Molecular and Subcellular Biology, 20: 161-166 (1998).

Cao, Y. "Therapeutic potentials of angiostatin in the treatment of cancer"; Haematologica, 84(7): 643-650 (1999).

Cao, Y. "Angiostatin: a plasminogen-related growth inhibitor"; Angiostatin—General discussion IV, pp. 247-251.

O'Reilly, M.S. et al. "Endogenous inhibitors of angiogenesis"; Proceedings of the American Association for Cancer Research, 37: 669 (1996) [Abstract].

O'Reilly, M.S. et al. "Angiostatin: A Circulating Endothelial Cell Inhibitor That Suppresses Angiogenesis and Tumor Growth"; Cold Spring Harbor Symposia on Quantitative Biology, LIX : 471-482 (1994).

Tanaka, T. et al. "Viral Vector-targeted Antiangiogenic Gene Therapy Utilizing an Angiostatin Complementary DNA"; Cancer Research, 58: 3362-3369 (1998).

Cao, Y. "Antiangiogenic gene therapy"; Gene Therapy and Regulation, 1(2): 123-139 (2000).

Cao, Y. "Endogenous angiogenesis inhibitors and their therapeutic implications"; The International Journal of Biochemistry & Cell Biology, 33: 357-369 (2001).

Cao, Y. et al. "Kringle 5 of Plasminogen is a Novel Inhibitor of Endothelial Cell Growth"; The Journal of Biological Chemistry, 272(36): 22924-22928 (1997).

O'Reilly, M.S. et al. "Angiostatin: A Novel angiogenesis Inhibitor That Mediates the Suppression of Metastases by a Lewis Lung Carcinoma"; Cell, 79: 315-328 (1994).

Wu, H-L, et al., "Interaction of Plasminogen and Fibrin in Plasminogen Activation", Journal of Biological Chemistry, 265:19658-19664 (1990).

Cao, Y., et al., "Kringle Domains of Human Angiostatin", Journal of Biological Chemistry, 271:29461-29467 (1996).

Forsgren, M., et al., "Molecular cloning and characterization of a full-length cDNA clone for human plasminogen", FEBS Letters 213:254-260 (1987).

Friezner, S.J., et al., "Characterization of the cDNA Coding for Mouse Plasminogen and Localization of the Gene to Mouse Chromosome 17", Genomics 8:49-61 (1990).

* cited by examiner

Figure 1

CATCCTGGGATT ... GACGGGAGACAG    linear

```
   1 CATCCTGGGATTGGGACCCACTTTCTGGGCACTGCTGGCCAGTCCCAAA ATG GAA CAT AAG GAA GTG GTT   70
   1                                                   M   E   H   K   E   V   V     7

71 CTT CTA CTT CTT TTA TTT CTG AAA TCA GGT CAA GGA GAG CCT CTG GAT GAC TAT GTG AAT  130
   8  L   L   L   L   L   F   L   K   S   G   Q   G   E   P   L   D   D   Y   V   N   27

131 ACC CAG GGG GCT TCA CTG TTC AGT GTC ACT AAG AAG CAG CTG GGA GCA GGA AGT ATA GAA  190
  28  T   Q   G   A   S   L   F   S   V   T   K   K   Q   L   G   A   G   S   I   E   47

191 GAA TGT GCA GCA AAA TGT GAG GAG GAC GAA GAA TTC ACC TGC AGG GCA TTC CAA TAT CAC  250
  48  E   C   A   A   K   C   E   E   D   E   E   F   T   C   R   A   F   Q   Y   H   67

251 AGT AAA GAG CAA CAA TGT GTG ATA ATG GCT GAA AAC AGG AAG TCC TCC ATA ATC ATT AGG  310
  68  S   K   E   Q   Q   C   V   I   M   A   E   N   R   K   S   S   I   I   I   R   87

311 ATG AGA GAT GTA GTT TTA TTT GAA AAG AAA GTG TAT CTC TCA GAG TGC AAG ACT GGG AAT  370
  88  M   R   D   V   V   L   F   E   K   K   V   Y   L   S   E   C   K   T   G   N  107

371 GGA AAG AAC TAC AGA GGG ACG ATG TCC AAA ACA AAA AAT GGC ATC ACC TGT CAA AAA TGG  430
 108  G   K   N   Y   R   G   T   M   S   K   T   K   N   G   I   T   C   Q   K   W  127

431 AGT TCC ACT TCT CCC CAC AGA CCT AGA TTC TCA CCT GCT ACA CAC CCC TCA GAG GGA CTG  490
 128  S   S   T   S   P   H   R   P   R   F   S   P   A   T   H   P   S   E   G   L  147

491 GAG GAG AAC TAC TGC AGG AAT CCA GAC AAC GAT CCG CAG GGG CCC TGG TGC TAT ACT ACT  550
 148  E   E   N   Y   C   R   N   P   D   N   D   P   Q   G   P   W   C   Y   T   T  167

551 GAT CCA GAA AAG AGA TAT GAC TAC TGC GAC ATT CTT GAG TGT GAA GAG GAA TGT ATG CAT  610
 168  D   P   E   K   R   Y   D   Y   C   D   I   L   E   C   E   E   E   C   M   H  187

611 TGC AGT GGA GAA AAC TAT GAC GGC AAA ATT TCC AAG ACC ATG TCT GGA CTG GAA TGC CAG  670
 188  C   S   G   E   N   Y   D   G   K   I   S   K   T   M   S   G   L   E   C   Q  207

671 GCC TGG GAC TCT CAG AGC CCA CAC GCT CAT GGA TAC ATT CCT TCC AAA TTT CCA AAC AAG  730
 208  A   W   D   S   Q   S   P   H   A   H   G   Y   I   P   S   K   F   P   N   K  227

731 AAC CTG AAG AAG AAT TAC TGT CGT AAC CCC GAT AGG GAG CTG CGG CCT TGG TGT TTC ACC  790
 228  N   L   K   K   N   Y   C   R   N   P   D   R   E   L   R   P   W   C   F   T  247

791 ACC GAC CCC AAC AAG CGC TGG GAA CTT TGT GAC ATC CCC CGC TGC ACA ACA CCT CCA CCA  850
 248  T   D   P   N   K   R   W   E   L   C   D   I   P   R   C   T   T   P   P   P  267

851 TCT TCT GGT CCC ACC TAC CAG TGT CTG AAG GGA ACA GGT GAA AAC TAT CGC GGG AAT GTG  910
 268  S   S   G   P   T   Y   Q   C   L   K   G   T   G   E   N   Y   R   G   N   V  287

911 GCT GTT ACC GTG TCC GGG CAC ACC TGT CAG CAC TGG AGT GCA CAG ACC CCT CAC ACA CAT  970
 288  A   V   T   V   S   G   H   T   C   Q   H   W   S   A   Q   T   P   H   T   H  307

971 AAC AGG ACA CCA GAA AAC TTC CCC TGC AAA AAT TTG GAT GAA AAC TAC TGC CGC AAT CCT 1030
 308  N   R   T   P   E   N   F   P   C   K   N   L   D   E   N   Y   C   R   N   P  327

1031 GAC GGA AAA AGG GCC CCA TGG TGC CAT ACA ACC AAC AGC CAA GTG CGG TGG GAG TAC TGT 1090
 328  D   G   K   R   A   P   W   C   H   T   T   N   S   Q   V   R   W   E   Y   C  347

1091 AAG ATA CCG TCC TGT GAC TCC TCC CCA GTA TCC ACG GAA CAA TTG GCT CCC ACA GCA CCA 1150
 348  K   I   P   S   C   D   S   S   P   V   S   T   E   Q   L   A   P   T   A   P  367

1151 CCT GAG CTA ACC CCT GTG GTC CAG GAC TGC TAC CAT GGT GAT GGA CAG AGC TAC CGA GGC 1210
 368  P   E   L   T   P   V   V   Q   D   C   Y   H   G   D   G   Q   S   Y   R   G  387

1211 ACA TCC TCC ACC ACC ACC ACA GGA AAG AAG TGT CAG TCT TGG TCA TCT ATG ACA CCA CAC 1270
 388  T   S   S   T   T   T   T   G   K   K   C   Q   S   W   S   S   M   T   P   H  407

1271 CGG CAC CAG AAG ACC CCA GAA AAC TAC CCA AAT GCT GGC CTG ACA ATG AAC TAC TGC AGG 1330
 408  R   H   Q   K   T   P   E   N   Y   P   N   A   G   L   T   M   N   Y   C   R  427

1331 AAT CCA GAT GCC GAT AAA GGC CCC TGG TGT TTT ACC ACA GAC CCC AGC GTC AGG TGG GAG 1390
 428  N   P   D   A   D   K   G   P   W   C   F   T   T   D   P   S   V   R   W   E  447

1391 TAC TGC AAC CTG AAA AAA TGC TCA GGA ACA GAA GCG AGT GTT GTA GCA CCT CCG CCT GTT 1450
 448  Y   C   N   L   K   K   C   S   G   T   E   A   S   V   V   A   P   P   P   V  467
```

Figure 1 Continued

```
1451 GTC CTG CTT CCA GAT GTA GAG ACT CCT TCC GAA GAA GAC TGT ATG TTT GGG AAT GGG AAA 1510
 468 V   L   L   P   D   V   E   T   P   S   E   E   D   C   M   F   G   N   G   K    487

1511 GGA TAC CGA GGC AAG AGG GCG ACC ACT GTT ACT GGG ACG CCA TGC CAG GAC TGG GCT GCC 1570
 488 G   Y   R   G   K   R   A   T   T   V   T   G   T   P   C   Q   D   W   A   A    507

1571 CAG GAG CCC CAT AGA CAC AGC ATT TTC ACT CCA GAG ACA AAT CCA CGG GCG GGT CTG GAA 1630
 508 Q   E   P   H   R   H   S   I   F   T   P   E   T   N   P   R   A   G   L   E    527

1631 AAA AAT TAC TGC CGT AAC CCT GAT GGT GAT GTA GGT GGT CCC TGG TGC TAC ACG ACA AAT 1690
 528 K   N   Y   C   R   N   P   D   G   D   V   G   G   P   W   C   Y   T   T   N    547

1691 CCA AGA AAA CTT TAC GAC TAC TGT GAT GTC CCT CAG TGT GCG GCC CCT TCA TTT GAT TGT 1750
 548 P   R   K   L   Y   D   Y   C   D   V   P   Q   C   A   A   P   S   F   D   C    567

1751 GGG AAG CCT CAA GTG GAG CCG AAG AAA TGT CCT GGA AGG GTT GTA GGG GGG TGT GTG GCC 1810
 568 G   K   P   Q   V   E   P   K   K   C   P   G   R   V   V   G   G   C   V   A    587

1811 CAC CCA CAT TCC TGG CCC TGG CAA GTC AGT CTT AGA ACA AGG TTT GGA ATG CAC TTC TGT 1870
 588 H   P   H   S   W   P   W   Q   V   S   L   R   T   R   F   G   M   H   F   C    607

1871 GGA GGC ACC TTG ATA TCC CCA GAG TGG GTG TTG ACT GCT GCC CAC TGC TTG GAG AAG TCC 1930
 608 G   G   T   L   I   S   P   E   W   V   L   T   A   A   H   C   L   E   K   S    627

1931 CCA AGG CCT TCA TCC TAC AAG GTC ATC CTG GGT GCA CAC CAA GAA GTG AAT CTC GAA CCG 1990
 628 P   R   P   S   S   Y   K   V   I   L   G   A   H   Q   E   V   N   L   E   P    647

1991 CAT GTT CAG GAA ATA GAA GTG TCT AGG CTG TTC TTG GAG CCC ACA CGA AAA GAT ATT GCC 2050
 648 H   V   Q   E   I   E   V   S   R   L   F   L   E   P   T   R   K   D   I   A    667

2051 TTG CTA AAG CTA AGC AGT CCT GCC GTC ATC ACT GAC AAA GTA ATC CCA GCT TGT CTG CCA 2110
 668 L   L   K   L   S   S   P   A   V   I   T   D   K   V   I   P   A   C   L   P    687

2111 TCC CCA AAT TAT GTG GTC GCT GAC CGG ACC GAA TGT TTC GTC ACT GGC TGG GGA GAA ACC 2170
 688 S   P   N   Y   V   V   A   D   R   T   E   C   F   V   T   G   W   G   E   T    707

2171 CAA GGT ACT TTT GGA GCT GGC CTT CTC AAG GAA GCC CAG CTC CCT GTG ATT GAG AAT AAA 2230
 708 Q   G   T   F   G   A   G   L   L   K   E   A   Q   L   P   V   I   E   N   K    727

2231 GTG TGC AAT CGC TAT GAG TTT CTG AAT GGA AGA GTC CAA TCC ACC GAA CTC TGT GCT GGG 2290
 728 V   C   N   R   Y   E   F   L   N   G   R   V   Q   S   T   E   L   C   A   G    747

2291 CAT TTG GCC GGA GGC ACT GAC AGT TGC CAG GGT GAC AGT GGA GGT CCT CTG GTT TGC TTC 2350
 748 H   L   A   G   G   T   D   S   C   Q   G   D   S   G   G   P   L   V   C   F    767

2351 GAG AAG GAC AAA TAC ATT TTA CAA GGA GTC ACT TCT TGG GGT CTT GGC TGT GCA CGC CCC 2410
 768 E   K   D   K   Y   I   L   Q   G   V   T   S   W   G   L   G   C   A   R   P    787

2411 AAT AAG CCT GGT GTC TAT GTT CGT GTT TCA AGG TTT GTT ACT TGG ATT GAG GGA GTG ATG 2470
 788 N   K   P   G   V   Y   V   R   V   S   R   F   V   T   W   I   E   G   V   M    807

2471 AGA AAT AAT TAA TTGGACGGGAGACAG                                                   2497
 808 R   N   N   *                                                                    811
```

```
  1 MEHKEVVLLL  LLFLKSGQGE  PLDDYVNTQG  ASLFSVTKKQ  LGAGSIEECA
 51 AKCEEDEEFT  CRAFQYHSKE  QQCVIMAENR  KSSIIIRMRD  VVLFEKKVYL
101 SECKTGNGKN  YRGTMSKTKN  GITCQKWSST  SPHRPRFSPA  THPSEGLEEN
151 YCRNPDNDPQ  GPWCYTTDPE  KRYDYCDILE  CEEECMHCSG  ENYDGKISKT
201 MSGLECQAWD  SQSPHAHGYI  PSKFPNKNLK  KNYCRNPDRE  LRPWCFTTDP
251 NKRWELCDIP  RCTTPPPSSG  PTYQCLKGTG  ENYRGNVAVT  VSGHTCQHWS
301 AQTPHTHNRT  PENFPCKNLD  ENYCRNPDGK  RAPWCHTTNS  QVRWEYCKIP
351 SCDSSPVSTE  QLAPTAPPEL  TPVVQDCYHG  DGQSYRGTSS  TTTTGKKCQS
401 WSSMTPHRHQ  KTPENYPNAG  LTMNYCRNPD  ADKGPWCFTT  DPSVRWEYCN
451 LKKCSGTEAS  VVAPPPVVLL  PDVETPSEED  CMFGNGKGYR  GKRATTVTVT
501 PCQDWAAQEP  HRHSIFTPET  NPRAGLEKNY  CRNPDGDVGG  PWCYTTNPRK
551 LYDYCDVPQC  AAPSFDCGKP  QVEPKKCPGR  VVGGCVAHPH  SWPWQVSLRT
601 RFGMHFCGGT  LISPEWVLTA  AHCLEKSPRP  SSYKVILGAH  QEVNLEPHGQ
651 EIEVSRLFLE  PTRKDIALLK  LSSPAVITDK  VIPACLPSPN  YVVADRTECF
701 ITGWGETQGT  FGAGLLKEAQ  LPVIENKVCN  RYEFLNGRVQ  STELCAGHLA
751 GGTDSCQGDS  GGPLVCFEKD  KYILQGVTSW  GLGCARPNKP  GVYVRVSRFV
801 TWIEGVMRNN
```

Figure 2

Amino acid sequence of human Kringle 1-5 of plasminogen

K1　K2　K3　K4　K5

CKTGNGKNYRGTMSKTKNGITCQKWSSTSPHRPRFSPATH
PSEGLEENYCRNPDNDPQGPWCYTTDPEKRYDYCDILECE
EECMHCSGENYDGKISKTMSGLECQAWDSQSPHAHGYIPS
KFPNKNLKKNYCRNPDRELRPWCFTTDPNKRWELCDIPRCT
TPPPSSGPTYQCLKGTGENYRGNVAVTVSGHTCQHWSAQT
PHTHNRTPENFPCKNLDENYCRNPDGKRAPWCHTFNSQVR
WEYCKIPSCDSSPVSTEQLAPTAPPELTPVVQDCYHGDGQS
YRGTSSTTTTGKKCQSWSSMTPHRHQKTPENYPNAGLTMN
YCRNPDADKGPWCFTTDPSVRWEYCNLKKCSGTEASVVAP
PPVVLLPDVETPSEEDCMFGNGKGYRGKRATTVTGTPCQD
WAAQEPHRHSIFTPETNPRAGLEKNYCRNPDGDVGGPWCY
TTNPRKLYDYCDVPQC

Figure 5

Construct 1

Construct 2

SEQUENCE LISTING

```
<160> NUMBER OF SEQ ID NOS: 11

<210> SEQ ID NO 1
<211> LENGTH: 2497
<212> TYPE: DNA
<213> ORGANISM: Homo sapiens
<220> FEATURE:
<221> NAME/KEY: CDS
<222> LOCATION: (50)..(2482)

<400> SEQUENCE: 1
catcctggga ttgggaccca ctttctgggc actgctggcc agtcccaaa atg gaa cat        58
                                                      Met Glu His
                                                        1 aag gaa gtg gtt ctt cta ctt ctt tta ttt ctg aaa tca ggt caa gga        106
Lys Glu Val Val Leu Leu Leu Leu Leu Phe Leu Lys Ser Gly Gln Gly
      5                   10                  15 gag cct ctg gat gac tat gtg aat acc cag ggg gct tca ctg ttc agt        154
Glu Pro Leu Asp Asp Tyr Val Asn Thr Gln Gly Ala Ser Leu Phe Ser
 20                  25                  30                  35 gtc act aag aag cag ctg gga gca gga agt ata gaa gaa tgt gca gca        202
Val Thr Lys Lys Gln Leu Gly Ala Gly Ser Ile Glu Glu Cys Ala Ala
                 40                  45                  50 aaa tgt gag gag gac gaa gaa ttc acc tgc agg gca ttc caa tat cac        250
Lys Cys Glu Glu Asp Glu Glu Phe Thr Cys Arg Ala Phe Gln Tyr His
             55                  60                  65 agt aaa gag caa caa tgt gtg ata atg gct gaa aac agg aag tcc tcc        298
Ser Lys Glu Gln Gln Cys Val Ile Met Ala Glu Asn Arg Lys Ser Ser
         70                  75                  80 ata atc att agg atg aga gat gta gtt tta ttt gaa aag aaa gtg tat        346
Ile Ile Ile Arg Met Arg Asp Val Val Leu Phe Glu Lys Lys Val Tyr
     85                  90                  95 ctc tca gag tgc aag act ggg aat gga aag aac tac aga ggg acg atg        394
Leu Ser Glu Cys Lys Thr Gly Asn Gly Lys Asn Tyr Arg Gly Thr Met
```

|                                                                                      |      |
|--------------------------------------------------------------------------------------|------|
| tcc aaa aca aaa aat ggc atc acc tgt caa aaa tgg agt tcc act tct                      | 442  |
| Ser Lys Thr Lys Asn Gly Ile Thr Cys Gln Lys Trp Ser Ser Thr Ser                      |      |
|         100             105             110             115                          |      |
|                     120                             125             130              |      |
| ccc cac aga cct aga ttc tca cct gct aca cac ccc tca gag gga ctg                      | 490  |
| Pro His Arg Pro Arg Phe Ser Pro Ala Thr His Pro Ser Glu Gly Leu                      |      |
|             135                         140                         145              |      |
| gag gag aac tac tgc agg aat cca gac aac gat ccg cag ggg ccc tgg                      | 538  |
| Glu Glu Asn Tyr Cys Arg Asn Pro Asp Asn Asp Pro Gln Gly Pro Trp                      |      |
|                 150                             155                 160              |      |
| tgc tat act act gat cca gaa aag aga tat gac tac tgc gac att ctt                      | 586  |
| Cys Tyr Thr Thr Asp Pro Glu Lys Arg Tyr Asp Tyr Cys Asp Ile Leu                      |      |
|         165                             170                 175                      |      |
| gag tgt gaa gag gaa tgt atg cat tgc agt gga gaa aac tat gac ggc                      | 634  |
| Glu Cys Glu Glu Glu Cys Met His Cys Ser Gly Glu Asn Tyr Asp Gly                      |      |
| 180                             185                             195                  |      |
| aaa att tcc aag acc atg tct gga ctg gaa tgc cag gcc tgg gac tct                      | 682  |
| Lys Ile Ser Lys Thr Met Ser Gly Leu Glu Cys Gln Ala Trp Asp Ser                      |      |
|                         200                         205                 210          |      |
| cag agc cca cac gct cat gga tac att cct tcc aaa ttt cca aac aag                      | 730  |
| Gln Ser Pro His Ala His Gly Tyr Ile Pro Ser Lys Phe Pro Asn Lys                      |      |
|             215                             220                 225                  |      |
| aac ctg aag aag aat tac tgt cgt aac ccc gat agg gag ctg cgg cct                      | 778  |
| Asn Leu Lys Lys Asn Tyr Cys Arg Asn Pro Asp Arg Glu Leu Arg Pro                      |      |
|                 230                             235                 240              |      |
| tgg tgt ttc acc acc gac ccc aac aag cgc tgg gaa ctt tgt gac atc                      | 826  |
| Trp Cys Phe Thr Thr Asp Pro Asn Lys Arg Trp Glu Leu Cys Asp Ile                      |      |
|         245                             250                         255              |      |
| ccc cgc tgc aca aca cct cca cca tct tct ggt ccc acc tac cag tgt                      | 874  |
| Pro Arg Cys Thr Thr Pro Pro Pro Ser Ser Gly Pro Thr Tyr Gln Cys                      |      |
| 260                         265                         270                 275      |      |
| ctg aag gga aca ggt gaa aac tat cgc ggg aat gtg gct gtt acc gtg                      | 922  |
| Leu Lys Gly Thr Gly Glu Asn Tyr Arg Gly Asn Val Ala Val Thr Val                      |      |
|                     280                         285                 290              |      |
| tcc ggg cac acc tgt cag cac tgg agt gca cag acc cct cac aca cat                      | 970  |
| Ser Gly His Thr Cys Gln His Trp Ser Ala Gln Thr Pro His Thr His                      |      |
|             295                         300                         305              |      |
| aac agg aca cca gaa aac ttc ccc tgc aaa aat ttg gat gaa aac tac                      | 1018 |
| Asn Arg Thr Pro Glu Asn Phe Pro Cys Lys Asn Leu Asp Glu Asn Tyr                      |      |
|                 310                             315                 320              |      |
| tgc cgc aat cct gac gga aaa agg gcc cca tgg tgc cat aca acc aac                      | 1066 |
| Cys Arg Asn Pro Asp Gly Lys Arg Ala Pro Trp Cys His Thr Thr Asn                      |      |
|         325                             330                         335              |      |
| agc caa gtg cgg tgg gag tac tgt aag ata ccg tcc tgt gac tcc tcc                      | 1114 |
| Ser Gln Val Arg Trp Glu Tyr Cys Lys Ile Pro Ser Cys Asp Ser Ser                      |      |
| 340                             345                         350             355      |      |
| cca gta tcc acg gaa caa ttg gct ccc aca gca cca cct gag cta acc                      | 1162 |
| Pro Val Ser Thr Glu Gln Leu Ala Pro Thr Ala Pro Pro Glu Leu Thr                      |      |
|                     360                             365                 370          |      |
| cct gtg gtc cag gac tgc tac cat ggt gat gga cag agc tac cga ggc                      | 1210 |
| Pro Val Val Gln Asp Cys Tyr His Gly Asp Gly Gln Ser Tyr Arg Gly                      |      |
|             375                             380                     385              |      |
| aca tcc tcc acc acc acc aca gga aag aag tgt cag tct tgg tca tct                      | 1258 |
| Thr Ser Ser Thr Thr Thr Thr Gly Lys Lys Cys Gln Ser Trp Ser Ser                      |      |
|                 390                             395                 400              |      |
| atg aca cca cac cgg cac cag aag acc cca gaa aac tac cca aat gct                      | 1306 |
| Met Thr Pro His Arg His Gln Lys Thr Pro Glu Asn Tyr Pro Asn Ala                      |      |
|         405                             410                         415              |      |
| ggc ctg aca atg aac tac tgc agg aat cca gat gcc gat aaa ggc ccc                      | 1354 |

-continued

| | | | | | | | | | | | | | | | | |
|---|---|---|---|---|---|---|---|---|---|---|---|---|---|---|---|---|
| | Gly | Leu | Thr | Met | Asn | Tyr | Cys | Arg | Asn | Pro | Asp | Ala | Asp | Lys | Gly | Pro |
| | 420 | | | | 425 | | | | 430 | | | | 435 | | | |

```
tgg tgt ttt acc aca gac ccc agc gtc agg tgg gag tac tgc aac ctg      1402
Trp Cys Phe Thr Thr Asp Pro Ser Val Arg Trp Glu Tyr Cys Asn Leu
            440                 445                 450 aaa aaa tgc tca gga aca gaa gcg agt gtt gta gca cct ccg cct gtt      1450
Lys Lys Cys Ser Gly Thr Glu Ala Ser Val Val Ala Pro Pro Pro Val
                455                 460                 465 gtc ctg ctt cca gat gta gag act cct tcc gaa gaa gac tgt atg ttt      1498
Val Leu Leu Pro Asp Val Glu Thr Pro Ser Glu Glu Asp Cys Met Phe
        470                 475                 480 ggg aat ggg aaa gga tac cga ggc aag agg gcg acc act gtt act ggg      1546
Gly Asn Gly Lys Gly Tyr Arg Gly Lys Arg Ala Thr Thr Val Thr Gly
    485                 490                 495 acg cca tgc cag gac tgg gct gcc cag gag ccc cat aga cac agc att      1594
Thr Pro Cys Gln Asp Trp Ala Ala Gln Glu Pro His Arg His Ser Ile
500                 505                 510                 515 ttc act cca gag aca aat cca cgg gcg ggt ctg gaa aaa aat tac tgc      1642
Phe Thr Pro Glu Thr Asn Pro Arg Ala Gly Leu Glu Lys Asn Tyr Cys
                520                 525                 530 cgt aac cct gat ggt gat gta ggt ggt ccc tgg tgc tac acg aca aat      1690
Arg Asn Pro Asp Gly Asp Val Gly Gly Pro Trp Cys Tyr Thr Thr Asn
            535                 540                 545 cca aga aaa ctt tac gac tac tgt gat gtc cct cag tgt gcg gcc cct      1738
Pro Arg Lys Leu Tyr Asp Tyr Cys Asp Val Pro Gln Cys Ala Ala Pro
        550                 555                 560 tca ttt gat tgt ggg aag cct caa gtg gag ccg aag aaa tgt cct gga      1786
Ser Phe Asp Cys Gly Lys Pro Gln Val Glu Pro Lys Lys Cys Pro Gly
565                 570                 575 agg gtt gta ggg ggg tgt gtg gcc cac cca cat tcc tgg ccc tgg caa      1834
Arg Val Val Gly Gly Cys Val Ala His Pro His Ser Trp Pro Trp Gln
580                 585                 590                 595 gtc agt ctt aga aca agg ttt gga atg cac ttc tgt gga ggc acc ttg      1882
Val Ser Leu Arg Thr Arg Phe Gly Met His Phe Cys Gly Gly Thr Leu
                600                 605                 610 ata tcc cca gag tgg gtg ttg act gct gcc cac tgc ttg gag aag tcc      1930
Ile Ser Pro Glu Trp Val Leu Thr Ala Ala His Cys Leu Glu Lys Ser
            615                 620                 625 cca agg cct tca tcc tac aag gtc atc ctg ggt gca cac caa gaa gtg      1978
Pro Arg Pro Ser Ser Tyr Lys Val Ile Leu Gly Ala His Gln Glu Val
        630                 635                 640 aat ctc gaa ccg cat gtt cag gaa ata gaa gtg tct agg ctg ttc ttg      2026
Asn Leu Glu Pro His Val Gln Glu Ile Glu Val Ser Arg Leu Phe Leu
    645                 650                 655 gag ccc aca cga aaa gat att gcc ttg cta aag cta agc agt cct gcc      2074
Glu Pro Thr Arg Lys Asp Ile Ala Leu Leu Lys Leu Ser Ser Pro Ala
660                 665                 670                 675 gtc atc act gac aaa gta atc cca gct tgt ctg cca tcc cca aat tat      2122
Val Ile Thr Asp Lys Val Ile Pro Ala Cys Leu Pro Ser Pro Asn Tyr
                680                 685                 690 gtg gtc gct gac cgg acc gaa tgt ttc atc act ggc tgg gga gaa acc      2170
Val Val Ala Asp Arg Thr Glu Cys Phe Ile Thr Gly Trp Gly Glu Thr
            695                 700                 705 caa ggt act ttt gga gct ggc ctt ctc aag gaa gcc cag ctc cct gtg      2218
Gln Gly Thr Phe Gly Ala Gly Leu Leu Lys Glu Ala Gln Leu Pro Val
        710                 715                 720 att gag aat aaa gtg tgc aat cgc tat gag ttt ctg aat gga aga gtc      2266
Ile Glu Asn Lys Val Cys Asn Arg Tyr Glu Phe Leu Asn Gly Arg Val
725                 730                 735
```

-continued

```
caa tcc acc gaa ctc tgt gct ggg cat ttg gcc gga ggc act gac agt       2314
Gln Ser Thr Glu Leu Cys Ala Gly His Leu Ala Gly Gly Thr Asp Ser
740             745                 750                 755 tgc cag ggt gac agt gga ggt cct ctg gtt tgc ttc gag aag gac aaa       2362
Cys Gln Gly Asp Ser Gly Gly Pro Leu Val Cys Phe Glu Lys Asp Lys
                760                 765                 770 tac att tta caa gga gtc act tct tgg ggt ctt ggc tgt gca cgc ccc       2410
Tyr Ile Leu Gln Gly Val Thr Ser Trp Gly Leu Gly Cys Ala Arg Pro
            775                 780                 785 aat aag cct ggt gtc tat gtt cgt gtt tca agg ttt gtt act tgg att       2458
Asn Lys Pro Gly Val Tyr Val Arg Val Ser Arg Phe Val Thr Trp Ile
        790                 795                 800 gag gga gtg atg aga aat aat taa ttggacggga gacag                       2497
Glu Gly Val Met Arg Asn Asn
    805             810

<210> SEQ ID NO 2
<211> LENGTH: 810
<212> TYPE: PRT
<213> ORGANISM: Homo sapiens

<400> SEQUENCE: 2

Met Glu His Lys Glu Val Val Leu Leu Leu Leu Phe Leu Lys Ser
 1               5                  10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270
```

```
Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                    325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
```

```
                  690                695                700
Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic

<400> SEQUENCE: 3

Val Pro Gln Cys Ala Ala His His His His His
 1               5                  10

<210> SEQ ID NO 4
<211> LENGTH: 458
<212> TYPE: PRT
<213> ORGANISM: Homo sapiens

<400> SEQUENCE: 4

Cys Lys Thr Gly Asn Gly Lys Asn Tyr Arg Gly Thr Met Ser Lys Thr
 1               5                  10                  15

Lys Asn Gly Ile Thr Cys Gln Lys Trp Ser Ser Thr Ser Pro His Arg
                20                  25                  30

Pro Arg Phe Ser Pro Ala Thr His Pro Ser Glu Gly Leu Glu Glu Asn
            35                  40                  45

Tyr Cys Arg Asn Pro Asp Asn Asp Pro Gln Gly Pro Trp Cys Tyr Thr
        50                  55                  60

Thr Asp Pro Glu Lys Arg Tyr Asp Tyr Cys Asp Ile Leu Glu Cys Glu
 65                 70                  75                  80

Glu Glu Cys Met His Cys Ser Gly Glu Asn Tyr Asp Gly Lys Ile Ser
                85                  90                  95

Lys Thr Met Ser Gly Leu Glu Cys Gln Ala Trp Asp Ser Gln Ser Pro
                100                 105                 110

His Ala His Gly Tyr Ile Pro Ser Lys Phe Pro Asn Lys Asn Leu Lys
            115                 120                 125

Lys Asn Tyr Cys Arg Asn Pro Asp Arg Glu Leu Arg Pro Trp Cys Phe
        130                 135                 140

Thr Thr Asp Pro Asn Lys Arg Trp Glu Leu Cys Asp Ile Pro Arg Cys
145                 150                 155                 160

Thr Thr Pro Pro Pro Ser Ser Gly Pro Thr Tyr Gln Cys Leu Lys Gly
                165                 170                 175

Thr Gly Glu Asn Tyr Arg Gly Asn Val Ala Val Thr Val Ser Gly His
                180                 185                 190
```

```
Thr Cys Gln His Trp Ser Ala Gln Thr Pro His Thr His Asn Arg Thr
            195                 200                 205

Pro Glu Asn Phe Pro Cys Lys Asn Leu Asp Glu Asn Tyr Cys Arg Asn
        210                 215                 220

Pro Asp Gly Lys Arg Ala Pro Trp Cys His Thr Asn Ser Gln Val
225                 230                 235                 240

Arg Trp Glu Tyr Cys Lys Ile Pro Ser Cys Asp Ser Ser Pro Val Ser
                245                 250                 255

Thr Glu Gln Leu Ala Pro Thr Ala Pro Pro Glu Leu Thr Pro Val Val
            260                 265                 270

Gln Asp Cys Tyr His Gly Asp Gly Gln Ser Tyr Arg Gly Thr Ser Ser
        275                 280                 285

Thr Thr Thr Thr Gly Lys Lys Cys Gln Ser Trp Ser Ser Met Thr Pro
        290                 295                 300

His Arg His Gln Lys Thr Pro Glu Asn Tyr Pro Asn Ala Gly Leu Thr
305                 310                 315                 320

Met Asn Tyr Cys Arg Asn Pro Asp Ala Asp Lys Gly Pro Trp Cys Phe
                325                 330                 335

Thr Thr Asp Pro Ser Val Arg Trp Glu Tyr Cys Asn Leu Lys Lys Cys
            340                 345                 350

Ser Gly Thr Glu Ala Ser Val Val Ala Pro Pro Val Val Leu Leu
        355                 360                 365

Pro Asp Val Glu Thr Pro Ser Glu Glu Asp Cys Met Phe Gly Asn Gly
370                 375                 380

Lys Gly Tyr Arg Gly Lys Arg Ala Thr Thr Val Thr Gly Thr Pro Cys
385                 390                 395                 400

Gln Asp Trp Ala Ala Gln Glu Pro His Arg His Ser Ile Phe Thr Pro
                405                 410                 415

Glu Thr Asn Pro Arg Ala Gly Leu Glu Lys Asn Tyr Cys Arg Asn Pro
            420                 425                 430

Asp Gly Asp Val Gly Gly Pro Trp Cys Tyr Thr Thr Asn Pro Arg Lys
        435                 440                 445

Leu Tyr Asp Tyr Cys Asp Val Pro Gln Cys
450                 455

<210> SEQ ID NO 5
<211> LENGTH: 568
<212> TYPE: PRT
<213> ORGANISM: Artificial Sequence
<220> FEATURE:
<223> OTHER INFORMATION: Description of Artificial Sequence:
      Angioquiescin

<400> SEQUENCE: 5

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
```

```
                    85                  90                  95
Lys Val Tyr Leu Ser Glu Cys Lys Thr Gly Asn Gly Lys Asn Tyr Arg
                100                 105                 110
Gly Thr Met Ser Lys Thr Lys Asn Gly Ile Thr Cys Gln Lys Trp Ser
            115                 120                 125
Ser Thr Ser Pro His Arg Pro Arg Phe Ser Pro Ala Thr His Pro Ser
        130                 135                 140
Glu Gly Leu Glu Glu Asn Tyr Cys Arg Asn Pro Asp Asn Asp Pro Gln
145                 150                 155                 160
Gly Pro Trp Cys Tyr Thr Thr Asp Pro Glu Lys Arg Tyr Asp Tyr Cys
                165                 170                 175
Asp Ile Leu Glu Cys Glu Glu Glu Cys Met His Cys Ser Gly Glu Asn
                180                 185                 190
Tyr Asp Gly Lys Ile Ser Lys Thr Met Ser Gly Leu Glu Cys Gln Ala
            195                 200                 205
Trp Asp Ser Gln Ser Pro His Ala His Gly Tyr Ile Pro Ser Lys Phe
        210                 215                 220
Pro Asn Lys Asn Leu Lys Lys Asn Tyr Cys Arg Asn Pro Asp Arg Glu
225                 230                 235                 240
Leu Arg Pro Trp Cys Phe Thr Thr Asp Pro Asn Lys Arg Trp Glu Leu
                245                 250                 255
Cys Asp Ile Pro Arg Cys Thr Thr Pro Pro Ser Ser Gly Pro Thr
                260                 265                 270
Tyr Gln Cys Leu Lys Gly Thr Gly Glu Asn Tyr Arg Gly Asn Val Ala
            275                 280                 285
Val Thr Val Ser Gly His Thr Cys Gln His Trp Ser Ala Gln Thr Pro
        290                 295                 300
His Thr His Asn Arg Thr Pro Glu Asn Phe Pro Cys Lys Asn Leu Asp
305                 310                 315                 320
Glu Asn Tyr Cys Arg Asn Pro Asp Gly Lys Arg Ala Pro Trp Cys His
                325                 330                 335
Thr Thr Asn Ser Gln Val Arg Trp Glu Tyr Cys Lys Ile Pro Ser Cys
                340                 345                 350
Asp Ser Ser Pro Val Ser Thr Glu Gln Leu Ala Pro Thr Ala Pro Pro
            355                 360                 365
Glu Leu Thr Pro Val Val Gln Asp Cys Tyr His Gly Asp Gly Gln Ser
        370                 375                 380
Tyr Arg Gly Thr Ser Ser Thr Thr Thr Thr Gly Lys Lys Cys Gln Ser
385                 390                 395                 400
Trp Ser Ser Met Thr Pro His Arg His Gln Lys Thr Pro Glu Asn Tyr
                405                 410                 415
Pro Asn Ala Gly Leu Thr Met Asn Tyr Cys Arg Asn Pro Asp Ala Asp
            420                 425                 430
Lys Gly Pro Trp Cys Phe Thr Thr Asp Pro Ser Val Arg Trp Glu Tyr
        435                 440                 445
Cys Asn Leu Lys Lys Cys Ser Gly Thr Glu Ala Ser Val Val Ala Pro
    450                 455                 460
Pro Pro Val Val Leu Leu Pro Asp Val Glu Thr Pro Ser Glu Glu Asp
465                 470                 475                 480
Cys Met Phe Gly Asn Gly Lys Gly Tyr Arg Gly Lys Arg Ala Thr Thr
                485                 490                 495
Val Thr Gly Thr Pro Cys Gln Asp Trp Ala Ala Gln Glu Pro His Arg
            500                 505                 510
```

```
His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
        530                 535                 540

Thr Thr Asn Pro Arg Lys Leu Tyr Asp Tyr Cys Asp Val Pro Gln Cys
545                 550                 555                 560

Ala Ala His His His His His His
                565

<210> SEQ ID NO 6
<211> LENGTH: 575
<212> TYPE: PRT
<213> ORGANISM: Artificial Sequence
<220> FEATURE:
<223> OTHER INFORMATION: Description of Artificial Sequence:
      Angioquiescin with a tumor targeting signal

<400> SEQUENCE: 6

Met Glu His Lys Glu Val Val Leu Leu Leu Leu Phe Leu Lys Ser
 1               5                  10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
```

```
                   290                 295                 300
His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
                340                 345                 350

Asp Ser Ser Pro Val Ser Thr Glu Gln Leu Ala Pro Thr Ala Pro Pro
                355                 360                 365

Glu Leu Thr Pro Val Val Gln Asp Cys Tyr His Gly Asp Gly Gln Ser
370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
                420                 425                 430

Lys Gly Pro Trp Cys Phe Thr Thr Asp Pro Ser Val Arg Trp Glu Tyr
                435                 440                 445

Cys Asn Leu Lys Lys Cys Ser Gly Thr Glu Ala Ser Val Val Ala Pro
450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
                500                 505                 510

His Ser Ile Phe Thr Pro Glu Thr Asn Pro Arg Ala Gly Leu Glu Lys
                515                 520                 525

Asn Tyr Cys Arg Asn Pro Asp Gly Asp Val Gly Gly Pro Trp Cys Tyr
                530                 535                 540

Thr Thr Asn Pro Arg Lys Leu Tyr Asp Tyr Cys Asp Val Pro Gln Cys
545                 550                 555                 560

Ala Ala Cys Asn Gly Arg Cys Val Ser Gly Cys Ala Gly Cys Arg
                565                 570                 575

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Tumor
      targeting signal

<400> SEQUENCE: 7

Cys Asn Gly Arg Cys Val Ser Gly Cys Ala Gly Cys Arg
  1               5                  10

<210> SEQ ID NO 8
<211> LENGTH: 570
<212> TYPE: PRT
<213> ORGANISM: Artificial Sequence
<220> FEATURE:
<223> OTHER INFORMATION: Description of Artificial Sequence:
      Angioquiescin with a tumor targeting signal peptide

<400> SEQUENCE: 8

Met Glu His Lys Glu Val Val Leu Leu Leu Leu Leu Phe Leu Lys Ser
```

-continued

```
  1               5              10              15
Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
            35                  40                  45

Cys Ala Ala Lys Cys Glu Glu Asp Glu Glu Phe Thr Cys Arg Ala Phe
            50                  55                  60

Gln Tyr His Ser Lys Glu Gln Gln Cys Val Ile Met Ala Glu Asn Arg
 65                  70                  75                  80

Lys Ser Ser Ile Ile Ile Arg Met Arg Asp Val Val Leu Phe Glu Lys
                 85                  90                  95

Lys Val Tyr Leu Ser Glu Cys Lys Thr Gly Asn Gly Lys Asn Tyr Arg
                100                 105                 110

Gly Thr Met Ser Lys Thr Lys Asn Gly Ile Thr Cys Gln Lys Trp Ser
                115                 120                 125

Ser Thr Ser Pro His Arg Pro Arg Phe Ser Pro Ala Thr His Pro Ser
            130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
            195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
                260                 265                 270

Tyr Gln Cys Leu Lys Gly Thr Gly Glu Asn Tyr Arg Gly Asn Val Ala
            275                 280                 285

Val Thr Val Ser Gly His Thr Cys Gln His Trp Ser Ala Gln Thr Pro
            290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Pro Val Ser Thr Glu Gln Leu Ala Pro Thr Ala Pro Pro
            355                 360                 365

Glu Leu Thr Pro Val Val Gln Asp Cys Tyr His Gly Asp Gly Gln Ser
            370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430
```

```
Lys Gly Pro Trp Cys Phe Thr Thr Asp Pro Ser Val Arg Trp Glu Tyr
            435                 440                 445

Cys Asn Leu Lys Lys Cys Ser Gly Thr Glu Ala Ser Val Val Ala Pro
        450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ala Cys Asp Arg Gly Asp Cys Phe Cys
                565                 570

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: Tumor
      targeting signal

<400> SEQUENCE: 9

Cys Asp Arg Gly Asp Cys Phe Cys
  1               5

<210> SEQ ID NO 10
<211> LENGTH: 12
<212> TYPE: DNA
<213> ORGANISM: Homo sapiens

<400> SEQUENCE: 10
catcctggga tt                                                           12

<210> SEQ ID NO 11
<211> LENGTH: 12
<212> TYPE: DNA
<213> ORGANISM: Homo sapiens

<400> SEQUENCE: 11
gacgggagac ag                                                           12
```

MATERIALS AND METHODS RELATING TO ENDOTHELIAL CELL GROWTH INHIBITORS

This application claims priority under 35 U.S.C. §119(e) to U.S. Provisional Application 60/230,893 filed Sep. 5, 2000, the entire disclosure of which is incorporated by reference herein.

FIELD OF THE INVENTION

The present invention concerns materials and methods relating to endothelial cell growth inhibitors. Particularly, but not exclusively, the present invention relates to the production and use of a recombinant protein or biologically active fragments thereof derived from mammalian plasminogen.

Further, the invention provides nucleic acid and amino acid sequence of the recombinant protein, as well as methods of introducing the nucleic acid sequence into cells so as to produce the secretable recombinant protein. The invention further provides the use of the recombinant protein for inhibiting angiogenesis.

BACKGROUND OF THE INVENTION

As used herein, the term "angiogenesis" means the generation of new blood vessels into a tissue or organ, and involves endothelial cell proliferation. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" means a thin layer of flat epithelial cells that lines serous cavities, lymph vessels and blood vessels.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Persistent, unregulated angiogenesis occurs in a multiplicity of disease states, e.g. tumor metastasis and abnormal growth by endothelial cells, and supports the pathological damage seen in these conditions. The diverse pathological disease states in which unregulated angiogenesis is present have been grouped together as angiogenic dependent or angiogenesis associated diseases.

The hypothesis that tumor growth is angiogenesis-dependent was first proposed in 1971. (Folkman J., Tumor angiogenesis: Therapeutic implications. *N. Engl. Jour. Med.* 285: 1182–1186, 1971). In its simplest terms it states: "Once tumor "take" has occurred, every increase in tumor cell population must be preceded by an increase in new capillaries converging on the tumor." Tumor "take" is currently understood to indicate a prevascular phase of tumor growth in which a population of tumor cells occupying a few cubic millimeters volume, and not exceeding a few million cells, can survive on existing host microvessels. Expansion of tumor volume beyond this phase requires the induction of new capillary blood vessels. For example, pulmonary micrometastases in the early prevascular phase in mice would be undetectable except by high power microscopy on histological sections.

Examples of the indirect evidence which support this concept include:

(1) The growth rate of tumors implanted in subcutaneous transparent chambers in mice is slow and linear before neovascularization, and rapid and nearly exponential after neovascularization. (Algire G H, et al. Vascular reactions of normal and malignant tumors in vivo. I. Vascular reactions of mice to wounds and to normal and neoplastic transplants.; *J Natl. Cancer Inst.* 6:73–85,1945).

(2) Tumors grown in isolated perfused organs where blood vessels do not proliferate are limited to 1–2 mm$^3$ but expand rapidly to >1000 times this volume when they are transplanted to mice and become neovascularized. (Folkman J, et al., Tumor behavior in isolated perfused organs: In vitro growth and metastasis of biopsy material in rabbit thyroid and canine intestinal segments. *Annals of Surgery* 164: 491–502, 1966).

(3) Tumor growth in the avascular cornea proceeds slowly and at a linear rate, but switches to exponential growth after neovascularization. (Gimbrone, M. A., Jr. et al., Tumor growth and neov ascularization: An experimental model using the rabbit cornea. *J. Natl. Cancer Institute* 52:41–427, 1974).

(4) Tumors suspended in the aqueous fluid of the anterior chamber of the rabbit eye, remain viable, avascular and limited in size to <1 mm$^3$. Once they are implanted on the iris vascular bed, they become neovascularized and grow rapidly, reaching 16,000 times their original volume within 2 weeks. (Gimbrone M A Jr., et al., Tumor dormancy in vivo by prevention of neovascularization, *J. Exp. Med.* 136: 261–276).

(5) When tumors are implanted on the chick embryo chorioallantoic membrane, they grow slowly during an avascular phase of >72 hours, but do not exceed a mean diameter of 0.93+0.29 mm. Rapid tumor expansion occurs within 24 hours after the onset of neovascularization, and by day 7 these vascularized tumors reach a mean diameter of 8.0+2.5 mm. (Knighton D., Avascular and vascular phases of tumor growth in the chick embryo. *British J. Cancer*, 35:347–356,1977).

(6) Vascular casts of metastases in the rabbit liver reveal heterogeneity in size of the metastases, but show a relatively uniform cut-off point for the size at which vascularization is present. Tumors are generally avascular up to 1 mm in diameter, but are neovascularized beyond that diameter. (Lien W., et al., The blood supply of experimental liver metastases. II. A microcirculatory study of normal and tumor vessels of the liver with the use of perfused silicone rubber. *Surgery* 68:334–340,1970).

(7) In transgenic mice which develop carcinomas in the beta cells of the pancreatic islets, pre-vascular hyperplastic islets are limited in size to <1 mm$^3$. At 6–7 weeks of age, 4–10% of the islets become neovascularized, and from these islets arise large vascularized tumors of more than 1000 times the volume of the pre-vascular islets. (Folkman J, et al., Induction of angioaenesis during the transition from hyperplasia to neoplasia. *Nature* 339:58–61,1989).

(8) A specific antibody against VEGF (vascular endothelial growth factor) reduces microvessel density and causes "significant or dramatic" inhibition of growth of three human tumors which rely on VEGF as their sole mediator of angiogenesis (in nude mice). The antibody does not inhibit growth of the tumor cells in vitro. (Kim K J, et al., Inhibition of vascular endothelial growth factor-induced angiogenesis suppresses tumor growth in vivo. *Nature* 362:841–844, 1993).

(9) Anti-bFGF monoclonal antibody causes 70% inhibition of growth of a mouse tumor which is dependent upon secretion of bFGF as its only mediator of angiogenesis. The antibody does not inhibit growth of the tumor cells in vitro. (Hori A, et al., Suppression of solid tumor growth by immunoneutralizing monoclonal antibody against human basic fibroblast growth factor. *Cancer Research*, 51:6180–6184, 1991).

(10) Intraperitoneal injection of bFGF enhances growth of a primary tumor and its metastases by stimulating growth of capillary endothelial cells in the tumor. The tumor cells themselves lack receptors for bFGF, and bFGF is not a mitogen for the tumor cells in vitro. (Gross J L, et al., Modulation of solid tumor growth in vivo by bFGF. *Proc. Amer. Assoc. Canc. Res.* 31: 79, 1990).

(11) A specific angiogenesis inhibitor (AGM-1470) inhibits tumor growth and metastases in vivo, but is much less active in inhibiting tumor cell proliferation in vitro. It inhibits vascular endothelial cell proliferation half-maximally at 4 logs lower concentration than it inhibits tumor cell proliferation. (Ingber D, et al., Anaioinhibins: Synthetic analogues of fumagillin which inhibit angiogenesis and suppress tumor growth. *Nature*, 48:555–557.1990). There is also indirect clinical evidence that tumor growth is angiogenesis dependent.

(12) Human retinoblastomas that are metastatic to the vitreous develop into avascular spheroids which are restricted to less than 1 mm$^3$ despite the fact that they are viable and incorporate 3H-thymidine (when removed from an enucleated eye and analyzed in vitro).

(13) Carcinoma of the ovary metastasizes to the peritoneal membrane as tiny avascular white seeds (1–3 mm$^3$). These implants rarely grow larger until one or more of them becomes neovascularized.

(14) Intensity of neovascularization in breast cancer (Weidner N, et al., Tumor angiogenesis correlates with metastasis in invasive breast carcinoma. N. Engl. J. Med. 324:1–8,1991, and Weidner N, et al., Tumor angioaenesis: A new significant and independent prognostic indicator in early-stage breast carcinoma, *J Natl. Cancer Inst.* 84:1875–1887, 1992) and in prostate cancer (Weidner N, Carroll P R, Flax J, Blumenfeld W, Folkman J. Tumor angiogenesis correlates with metastasis in invasive prostate carcinoma. American Journal of *Pathology*, 143(2):401–409,1993) correlates highly with risk of future metastasis.

(15) Metastasis from human cutaneous melanoma is rare prior to neovascularization. The onset of neovascularization leads to increased thickness of the lesion and an increasing risk of metastasis. (Srivastava A, et al., The prognostic significance of tumor vascularity in intermediate thickness (0.76–4.0 mm thick) skin melanoma. *Amer. J. Pathol.*133: 419–423,1988)

(16) In bladder cancer, the urinary level of an angiogenic peptide, bFGF, is a more sensitive indicator of status and extent of disease than is cytology. (Nguyen M, et al., Elevated levels of an angiogenic peptide, basic fibroblast growth factor, in urine of bladder cancer patients. *J. Natl. Cancer Inst.* 85:241–242,1993).

Thus, it is clear that angiogenesis plays a major role in the metastasis of a cancer. If this angiogenic activity could be repressed or eliminated, or otherwise controlled and modulated, then the tumor, although present, would not grow. In the disease state, prevention of angiogenesis could avert the damage caused by the invasion of the new microvascular system. Therapies directed at control of the angiogenic processes could lead to the abrogation or mitigation of these diseases.

Accordingly, within this field, there is a strong need for compositions and methods by which endothelial cell proliferation (such as the unwanted growth of blood vessels) especially into tumors, may be inhibited. There is also a need for methods for detecting, measuring and localizing such compositions. Such compositions should be able to help overcome the activity of endogenous growth factors in premetastatic tumors and inhibit the formation of the capillaries in the tumors, thereby inhibiting growth of the tumors. In addition, the compositions, fragments of such compositions and antibodies specific to said compositions, should be able to modulate the formation of capillaries in other angiogenic processes, such as wound healing and reproduction. Naturally, compositions and methods for inhibiting angiogenesis should preferably be non-toxic and produce few side effects. Also needed is a method for detecting, measuring and localizing the binding sites for the composition. The compositions and fragments of the compositions should be capable of being conjugated to other molecules for both radioactive and non-radioactive labeling purposes.

Some of the needs mentioned above have now been answered by important work that has been completed on the determination of a protein capable of modulating or regulating, e.g. inhibiting, the endothelial cell proliferation in vitro and angiogenesis in in vivo assays. See for example, PCT/SE98-01262, PCT/SE00/00719 (unpublished at time of filing) and Cao et al PNAS. USA Vol. 96, p5728–5733, May 1999. However, the present inventor has appreciated that more determinations are needed. For example, the disclosed inhibitor K1–5 was generated by plasmin-mediated proteolysis. Proteolytic enzymes are involved in generation of a number of endogenous angiogenesis inhibitors and it has been shown that urokinase-activated plasmin can process plasminogen to release an angiogenesis inhibitor, K1–5 (protease-activated kringles 1–5).

However, this proteolytic protein (proteolytic K1–5) cannot be secreted (exported) from cells. Thus, it is not possible for the nucleic acid coding this proteolytic protein to be introduced into cells or body tissues so that the protein can be expressed and secreted. This therefore limits the practical use of the protein with regard to its production and use in treatment.

SUMMARY OF THE INVENTION

At its most general, the present invention relates to materials and methods involved in the production or use of recombinant protein (herein named "angioquiescin") which is capable of being secreted from a cell.

The inventor, having appreciated the need for a recombinant, as opposed to proteolytic, endothelial cell proliferation inhibitor, attempted to produce such a protein using the sequence of human plasminogen. As a first step, the sequence encoding the secretory signal (SS) peptide was expressed in association with the sequence encoding K1–5. However, the inventor found that the protein produced was not capable of correctly folding and thus was not able to be secreted out of cells.

The inventor then decided to add sequence encoding the pre-activation (PA) peptide so that the construct now encoded SS/PA/K1–5 (see FIG. 3). The inventor found that the protein encoded by this sequence was secreted (exported) from cells and thus, by inference, must be correctly folded. These surprising results indicate that the presence of the pre-activation peptide is essential to the production of angioquiescin.

Thus, in a first aspect of the present invention there is provided a nucleic acid molecule encoding a recombinant endothelial cell growth inhibitor (angioquiescin). Preferably the nucleic acid molecule is derived from that encoding human plasminogen as shown in FIG. 1 (SEQ ID NO: 1) and comprises sequence encoding a secretory signal peptide and a pre-activation peptide in association with sequence encoding K1–5. The nucleic acid may be DNA, cDNA or RNA and preferably has at least 70% identity with the sequence shown in FIG. 1 (SEQ ID NO: 1), more preferably at least 80%, even more preferably at least 90% and even preferably at least 95% identity with the sequence shown in FIG. 1 (SEQ ID NO: 1).

Preferably, the nucleic acid sequence starts at nucleotide number 50 (or codon ATG) and finishes at nucleotide number 1733 (or codon GCC) inclusively as shown in FIG. 1 (SEQ ID NO: 1).

The invention further provides nucleic acid encoding an amino acid sequence having at least 70% identity with the amino acid sequence between amino acid 1 and amino acid 562 inclusively of FIG. 1 (SEQ ID NO: 1). Preferably, the amino acid sequence has at least 80, 85, 90, 95 or 100% identity with the amino acid sequence as shown in FIG. 1 (SEQ ID NO: 1).

The nucleic acid sequence according to the present invention may comprise additional (non-K1–5 sequence or non plasminogen sequence) sequence joined at either the 5' or the 3' ends. For example, it may be preferable to include sequence relating to a cell specific promoter or sequence relating an expression tag or even simply, sequence relating to specific restriction endonuclease cleavage sites. In one preferred embodiment of the present invention, there is provided amino acid sequence relating to the recombinant K1–5 protein but also further comprising sequence relating to a peptide tag so that the protein can be purified with ease.

Further, the nucleic acid may further comprise sequence encoding a tumour targeting peptide. This targeting peptide would be expressed in association with the recombinant K1–5 protein and, surprisingly, the inventor has found that such a tag does not affect the folding of the protein and thus the secretability is not altered. The addition of a tumour targeting peptide means that the protein can be concentrated into the tumour tissue to be treated following administration into the human or animal body. Examples of tumour targeting peptides can be seen in FIGS. 7 (SEQ ID NO: 6) and 8 (SEQ ID NO: 8) although others are well known to the skilled person.

The nucleic acid according to the present invention is preferably provided as an isolate, in isolated form and/or purified form, or free or substantially free of material with which it is naturally associated, such as free or substantially free of nucleic acid flanking the coding region, secretory signal region and pre-activation region of angioquiescin, except one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding angioquiescin can be readily prepared by the skilled person using the information and references contained herein and techniques known in the art (for example, see Sambrook, Fritsch and Maniatis, "Molecular Cloning, A Laboratory Manual," Cold Spring Harbor Laboratory Press, 1989, and Ausubel et al, Short Protocols in Molecular Biology, John Wiley and Sons, 1992). These techniques include (i) the use of the polymerase chain reaction (PCR) to amplify samples of such nucleic acid, e.g. from genomic sources, (ii) chemical synthesis, or (iii) preparing cDNA sequences. Modifications to the sequences encoding angioquiescin can be made, e.g. using site directed mutagenesis, to lead to the expression of modified K1–5 polypeptide or to take account of codon preference in the host cells used to express the nucleic acid. The amino acid sequence for human plasminogen is shown in FIG. 2 (SEQ ID NO: 2). The amino acid sequence for a K1–5 is illustrated in FIG. 5 (SEQ ID NO: 4)

In order to obtain expression of angioquiescin nucleic acid sequences, the sequences can be incorporated in a vector having control sequences operably linked to the angioquiescin nucleic acid to control its expression. The vectors may include other sequences such as promoters or enhancers to drive the expression of the inserted nucleic acid, and/or nucleic acid sequences so that the recombinant polypeptide is produced as a fusion, for example cell targeting peptides may be introduced. Angioquiescin can then be obtained by transforming the vectors into host cells in which the vector is functional, culturing the host cells so that the angioquiescin polypeptide is produced and recovering the polypeptide from the host cells or the surrounding medium. Prokaryotic and eukaryotic cells are used for this purpose in the art, including strains of E. coli, yeast, and eukaryotic cells such as COS or CHO cells. The choice of host cell can be used to control the properties of the angioquiescin polypeptide expressed in those cells, e.g. controlling where the polypeptide is deposited in the host cells or affecting properties such as its glycosylation.

The sequences referred to above may be modified by addition, substitution, insertion or deletion of one or more nucleotides, but preferably without abolition of ability to hybridise selectively with nucleic acid with the sequence shown in FIG. 1 (SEQ ID NO: 1), that is wherein the degree of homology of the oligonucleotide or polynucleotide with one of the sequences given is sufficiently high.

Such homology can be readily determined by use of one of the commercially or otherwise publicly available software packages. Algorithms and software suitable for use in aligning sequences for comparison and calculation of sequence homology or identity will be known to those skilled in the art. Significant examples of such tools are the Pearson and Lipman search based FAST and BLAST programs. Details of these may be found in Altschul et al (1990), J. Mol. Biol. 215: 403–10; Lipman D J and Pearson W R (1985) Science 227, p1435–41. Publically available details of BLAST may be found on the internet at www.ncbi.nlm.nih.gov/BLAST/blast-help. Thus such homology and identity percentages can be ascertained using commercially or publicly available software packages incorporating, for example, FASTA and BLASTn software or by computer servers on the internet. An example of the former is the GCG Wisconsin Software package while both Genbank (see www.ncbi.nlm.nih.gov/BLAST) and EMBL: (see www.embl-heidelberg.de/Blast2) offer internet services. Default settings are conveniently used.

By the term identity is meant that the stated percentage of the claimed amino acid sequence or base sequence is to be found in the reference sequence in the same relative positions when the sequences are optimally aligned, notwithstanding the fact that the sequences may have deletions or additions in certain positions requiring introduction of gaps to allow alignment of the highest percentage of amino acids or bases. Preferably the sequence are aligned by using 10 or less gaps, ie. the total number of gaps introduced into the two sequences when added together is 10 or less. The length of such gaps is not of particular importance as long as the anti-angiogenic activity is retained but generally will be no more than 10, and preferably no more than 5 amino acids, or 30 and preferably no more than 15 bases.

Preferred parameters for BLAST searches are the default values, ie. for EMBL Advanced Blast2: Blastp Matrix BLOSUMS, Filter default, Echofilter X, Expect 10, Cutoff default, Strand both, Descriptions 50, Alignments 50. For BLASTn defaults are again preferably used. GCG Wisconsin Package defaults are Gap Weight 12, Length weight 4. FASTDB parameters used for a further preferred method of homology calaculation are mismatch penalty=1.00, gap penalty=1.00, gap size penalty=0.33 and joining penalty=30.0.

Alternatively, nucleic acids having the appropriate level of sequence homology with the nucleic acid sequence encoding angioquiescin may be identified by using hybridization and washing conditions of appropriate stringency. For example, hybridizations may be performed, according to the method of Sambrook et al., (22) using a hybridization solution comprising: 5× SSC, 5× Denhardt's reagent, 0.5–1.0% SDS, 100 μg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2× SSC and 1% SDS; (2) 15 minutes at room temperature in 2× SSC and 0.1% SDS; (3) 30 minutes-1 hour at 37° C. in 1× SSC and 1% SDS; (4) 2 hours at 42–65° C. in 1× SSC and 1% SDS, changing the solution every 30 minutes.

One common formula for calculating the stringency conditions required to achieve hybridization between nucleic acid molecules of a specified sequence homology is (Sambrook et al., 1989):

$$T_m = 81.5° C. + 16.6 \text{Log}[\text{Na}+] + 0.41(\% \ G+C) - 0.63 \ (\% \ \text{formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C. Such a sequence would be considered substantially homologous to the nucleic acid sequence of the present invention. Stringency conditions are discussed further below.

A convenient way of producing a recombinant protein according to the present invention is to express nucleic acid encoding it, by use of the nucleic acid in an expression system. The use of expression system has reached an advanced degree of sophistication today.

Accordingly, the present invention also encompasses a method of making a protein (as disclosed), the method including expression from nucleic acid encoding the recombinant protein (generally nucleic acid according to the invention). This may conveniently be achieved by growing a host cell containing such a vector in culture, under appropriate conditions which cause or allow expression of the protein. Proteins may also be expressed in in vitro systems, such as reticulocyte lysate.

Systems for cloning and expression of a protein in a variety of different host cells are well known. Suitable host cells include bacteria, eukaryotic cells such as mammalian and yeast, and baculovirus systems. Mammalian cell lines available in the art for expression of a heterologous protein include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing nucleic acid as disclosed herein. The nucleic acid of the invention may be integrated into the genome (e.g. chromosome) of the host cell. Integration may be promoted by inclusion of sequences which promote recombination with the genome, in accordance with standard techniques. The nucleic acid may be on an extra-chromosomal vector within the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide is produced. As the polypeptide is expressed coupled to the secretory signal leader peptide and the pre-activation peptide it may be secreted from the cell into the culture medium. Following production by expression, a polypeptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid may take place in vivo by way of gene therapy, as discussed below.

Instead of, or as well as, being used for the production of a recombinant protein encoded by a transgene, host cells may be used as a nucleic acid factory to replicate the nucleic acid of interest in order to generate large amounts of it.

Multiple copies of nucleic acid of interest may be made within a cell when coupled to an amplifiable gene such as DHFR. Host cells transformed with nucleic acid of interest, or which are descended from host cells into which nucleic acid was introduced, may be cultured under suitable conditions, e.g. in a fermenter, taken from the culture and subjected to processing to purify the nucleic acid. Following purification, the nucleic acid or one or more fragments thereof may be used as desired.

The skilled person can use the techniques described herein and others well known in the art to produce large amounts of angioquiescin for use as pharmaceuticals, in the developments of drugs and for further study into its properties and role in vivo. Experimental work confirming the production of angioquiescin is set out in the Materials and Methods section below.

Thus, a further aspect of the present invention provides a recombinant protein called angioquiescin which has the amino acid sequence derived from FIGS. 1 or 2, which may be in isolated and/or purified form, free or substantially free of material with which it is naturally associated, such as other polypeptides or such as human polypeptides e.g. human plasminogen or (for example if produced by expression in a prokaryotic cell) lacking in native glycosylation, e.g. unglycosylated. Preferably, angioquiescin contains amino acid sequence of a secretory signal peptide and a pre-activation peptide derived from human plasminogen. Thus, preferably the recombinant protein has, or consists essentially of, the amino acid sequence as shown in FIG. 6 (SEQ ID NO: 5). Angioquiescin preferably has a molecular weight of between 55kD and 69kD, even more preferably has a molecular weight of about 65kD depending on glycosylation of the molecule.

Polypeptides which are amino acid sequence variants, alleles, derivatives or mutants of angioquiescin are also provided by the present invention. A polypeptide which is a variant, allele, derivative or mutant may have an amino acid sequence which differs from that given in FIG. 6 by one or more of addition, substitution, deletion and insertion of one or more amino acids. Preferred such polypeptides have anti-angiogenic activity and maintain the ability to fold correctly so that they can be secreted from the cell. This function and ability to fold may be determined by: immunological cross-reactivity with an antibody reactive the polypeptide for which the sequence is given in FIG. 6 (SEQ ID NO: 5); sharing an epitope with the polypeptide for which the amino acid sequence is shown in FIG. 6 (SEQ ID NO: 5) (as determined for example by immunological cross-reactivity between the two polypeptides); and its ability to be secreted (exported) from a cell. Anti-angiogenic activity may be determined using in vivo models. For example, the mouse corneal angiogenesis model, the chick chorioallantoic model, the tumour angiogenesis model, or the matri-gel model. See for example, (1) Jam R. K., K. Schlenger, M. Hockel, and F. Yuan. 1997. Quantitative angiogenesis assays: progress and problems. Nat. Med. 3:1203–1208; (2) Cao R., H. L. Wu, N. Veitonmaki, P. Linden, J. Farnebo, G. Y. Shi, and Y. Cao. 1999a. Suppression of angiogenesis and tumor growth by the inhibitor K1–5 generated by plasmin-mediated proteolysis. Proc. Nati. Acad. Sci. USA. 96:5728–5733; (3) Cao R., J. Farnebo, M. Kurimoto, and Y. Cao. 1999b. Interleukin-18 acts as an angiogenesis and tumor suppressor. FASEB J. 13:2195–2202; and (4) Cao Y., and R. Cao. 1999. Angiogenesis inhibited by drinking tea. Nature 398:381. It is important to note that anti-endothelial activity does not always mean antiangiogenesis although process of antigenesis requires endothelial cell proliferation.

A polypeptide which is an amino acid sequence variant, allele, derivative or mutant of the amino acid sequence shown in FIG. 6 (SEQ ID NO: 5) may comprise an amino acid sequence which shares greater than about 70%, greater than about 80%, greater than about 90% or greater than about 95%. The sequence may share greater than about 70% similarity, greater than about 80% similarity or greater than about 90% similarity with the amino acid sequence shown in FIG. 6 (SEQ ID NO: 5). Particular amino acid sequence variants may differ from that shown in FIG. 6 (SEQ ID NO: 5) by insertion, addition, substitution or deletion of 1 amino acid, 2, 3, 4, 5–10, 10–20 20–30, 30–50, or more than 50 amino acids.

In a further aspect of the invention, there is provided an isolated amino acid sequence of angioquiescin. Preferably, this sequence is derived from the amino acid sequence shown in FIG. 1 (SEQ ID NO: 1). In particular, its preferred that the sequence corresponds with the amino acid sequence shown between (and including) amino acid number 1 and 562 of FIG. 1 (SEQ ID NO: 1). In FIG. 1, four arrows are shown. The first relates to the Open Reading Frame (ORF) starting at ATG (on line 1) this is where the new recombinant protein begins, the second (line 31) is where the original enzymatic cleavage of plasminogen clipped the molecule; and the third (on line 1691) is where the original cleavage of plasminogen ended K1–5; and the fourth (line 1691) is where the recombinant angioquiescin ends).

Thus, it can be seen that angioquiescin is a larger molecule that the proteolytically cleaved K1–5. This is illustrated in FIG. 4.

Again, the amino acid sequence of the present invention may comprise additional amino acid sequence at either the N-terminal or the C-terminal or both. This sequence may, for example, relating to a peptide tag to aid in the purification of the protein, or it may relate to a tumour targeting peptide such that angioquiescin can be specifically directed to tumours.

In the present context, reference is made to FIG. 1 (SEQ ID NO: 1) and FIG. 2 (SEQ ID NO: 2;) which show the sequence to human plasminogen and to FIG. 5 (SEQ ID NO: 4) which shows a sequence for K1–5. However, as characterization of plasminogen kringle domains in the prior art have shown an essential homology between species, such as human, mouse, monkey, bovine and porcine species, in its broadest aspect, the present invention refer to the specifically given amino acid or its correspondence in other species, while specific embodiments of mouse and human could just as well be defined by suitable reference to said included sequence listing numbers. (For a reference to the characterization of K1–5 domains from various species, see e.g. Petros et al. *Eur. J. Biochem.* 170:549–63 (1988); Schaller et al. *Enzyme* 40:63–69 (1988); Ramesh et al. *Eur. J. Biochem.* 159:581–95 (1986); and Schaller et al. *Eur. J. Biochiem.* 149:267–278 (1985)).

A further important use of the angioquiescin polypeptides is in raising antibodies that have the property of specifically binding to the angioquiescin polypeptides, or fragments or active portions thereof.

The production of monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-239400. A hybridoma producing a monoclonal antibody may be subject to genetic mutation or other changes, which may or may not alter the binding specificity of antibodies produced.

The provision of the novel protein angioquiescin enables for the first time the production of antibodies able to bind it specifically. Accordingly, a further aspect of the present invention provides an antibody able to bind specifically to angioquiescin whose sequence is given in FIG. 6 (SEQ ID NO: 5). Such an antibody may be specific in the sense of being able to distinguish between the polypeptide it is able to bind and other human polypeptides, e.g. plasminogen or proteolytic Kringles 15, for which it has no or substantially no binding affinity (e.g. a binding affinity of about 1000* worse). Specific antibodies bind an epitope on the molecule which is either not present or is not accessible on other molecules. Antibodies according to the invention may be specific for a particular mutant, variant, allele or derivative polypeptide of angioquiescin as between that molecule and the angioquiescin shown in FIG. 6 (SEQ ID NO: 5). Antibodies are also useful in purifying the polypeptide or polypeptides to which they bind, e.g. following production by recombinant expression from encoding nucleic acid.

Preferred antibodies according to the invention are isolated, in the sense of being free from contaminants such as antibodies able to bind other polypeptides and/or free of serum components. Monoclonal antibodies are preferred for some purposes, though polyclonal antibodies are within the scope of the present invention.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al, Nature, 357: 80–82, 1992). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Example antibody fragments, capable of binding an antigen or other binding partner are the Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

Humanised antibodies in which CDRs from a non-human source are grafted onto human framework regions, typically with the alteration of some of the framework amino acid residues, to provide antibodies which are less immunogenic than the parent non-human antibodies, are also included within the present invention A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP-A-184187, GB-A-2188638 or EP-A-0239400. Cloning and expression of chimeric antibodies are described in EP-A-0120694 and EPA-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule.

One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The mode of determining binding is not a feature of the present invention and those skilled in the art are able to choose a suitable mode according to their preference and general knowledge.

Antibodies according to the present invention may be used in screening for the presence of angioquiescin, for example in a test sample containing cells or cell lysate as discussed, and may be used in purifying and/or isolating a polypeptide according to the present invention, for instance following production of the polypeptide by expression from encoding nucleic acid therefor.

The nucleic acid encoding angioquiescin or the recombinant protein itself may be used in the preparation of a composition for medical use. Accordingly, the invention particularly relates to compositions which are pharmaceutical or veterinary compositions, which are compositions of the invention which include one or more pharmaceutically acceptable carriers and/or excipients. The composition may be administered in a variety of unit dosage forms depending upon the method of administration, e.g parenteral, topical, oral or local administration, for prophylactic and/or therapeutic treatment. For example, unit dosage forms suitable for oral administration include powder, tablets, pills, capsules and lozenges. A variety of carriers may be used, such as aqueous carriers, e.g. buffered saline etc. These solutions are free of undesirable matter. The compositions may also include pharmaceutically acceptable auxiliary substances as required to approximate physiological conditions, such as pH adjusting and buffering agents, toxicity adjusting agents and the like, e.g. sodium acetate, sodium chloride, potassium chloride, calcium chloride etc. For parenterally administrable compositions, see e.g. Remington's Pharmaceutical Science, 15th ed., Mack Publishing Company, Easton, Pa. (1980). A composition, or preparation, according to the present invention may be administered in a much lower dosage and the use thereof is thus superior to that of known angiostatin compositions. Consequently, the use of a pharmaceutical preparation comprising the recombinant K1–5 proteins or peptide as described above when compared to use of angiostatin, is easier to administer due to the smaller amount needed, which smaller dose also results in a cheaper medicament.

In one embodiment of the invention, the composition comprises a protein according to the invention, which is capable of inhibiting cancer metastases. The half maximal concentration (EC50) of the agents, ie proteins according to the present invention for the inhibition of endothelial cell proliferation is typically about 50 pM, to be compared with the EC50 value for angiostatin, which is 100 nM. (See FIG. 9)

The present invention relates to a recombinant protein or nucleic acid encoding said protein wherein the sequence for K1–5 is derived from human plasminogen, murine plasminogen, bovine plasminogen, Rhesus plasminogen or porcine plasminogen. The protein, according to the present invention is preferably capable of inhibiting endothelial cell proliferation in in vitro assays. Such an assay is described in Materials and Methods.

As mentioned above, the invention provides a recombinant protein, nucleic acid encoding said protein or a composition comprising said nucleic acid or protein, for use as a medicament. In addition, the invention also relates to the use of a protein, nucleic acid or composition according to the invention as defined above for the manufacture of a medicament for modulating, e.g. inhibiting, endothelial cell proliferation, for example for treating angiogenesis associated conditions or diseases, such as tumor growth, e.g. cancer, diabetes etc.

Again as discussed above, the present invention provides nucleic acid such as DNA or RNA, encoding a peptide, polypeptide or protein molecule according to the invention. A cDNA sequence which is complementary to such a sequence is also encompassed. Thus, a further aspect of the invention is any nucleic acid which under stringent conditions hybridizes specifically to one of the above defined nucleic acids.

In the present context, the term hybridising specifically to refers to the binding, duplexing or hybridizing of a molecule only to a particular nucleotide sequence under stringent conditions when that sequence is present in a complex mixture of DNA or RNA. In the present context, the term "stringent conditions" refers to conditions, under which a probe will hybridize to its target sequence, but to no other sequences. Stringent conditions are sequence-dependent and will be different in different circumstances. The one skilled in this field will easily choose the suitable conditions in the present context. Generally, stringent conditions are selected to be about 5° C. lower than the thermal melting point ($T_m$) for the specific sequence at a defined ionic strength and pH. Typically, stringent conditions will be those in which the salt concentration is less than about 1.0 M Na ion, such as about 0.01–1.0 M, at a pH of about 7.0–8.3 and the temperature is between about 30° C. and 60° C., depending on the length of the nucleotide. Stringent conditions may also be achieved by the addition of destabilizing agents, such as formamide. Such a nucleotide according to the invention may be of any length in accordance with the above defined.

In a preferred embodiment of the invention standard stringency conditions are 2× SSC and high stringency conditions as 1× SSC (see Church and Gilbert, *Proc Nat Acad Sci* USA (1984) 81, 1991–1995 incorporated herein by reference).

The nucleic acids according to the invention are cloned or amplified by in vitro methods, such as polymerase chain reaction (PCR), the ligase chain reaction (LCR), the transcription-based amplification system (TAS), etc. A wide variety of cloning and in vitro amplification methods are well known to persons of skill, see e.g. Berger and Kimmel, Guide to Molecular Cloning Techniques, *Methods in Enzymology* 152 Academic Press, Inc., San Diego, Calif. (Berger); Sambrook et al., (1989) *Molecular Cloning—A Laboratory Manual*, vol 1–3, Cold Spring Harbor Laboratory, Cold Spring Harbor Press, N.Y.; Current Protocols in Molecular Biology, F. M. Ausbel et al., eds., Current Protocols; Cashion et al., U.S. Pat. No. 5,017,478; and Carr, EP patent no. 0 246 864.

A further aspect of the present invention is the use of a molecule as defined above, eg. a cDNA, in gene therapy as well as such gene therapy methods. The methods according to the invention can involve transfecting cells of a mammal with a vector expressing a recombinant protein according to the invention. The transfection can be in vivo or ex vivo. Ex vivo transfection is suitably followed by re-infusing the cells into the organism. Other methods involve administering to the mammal, e.g. a human, of a therapeutically effective dose of a composition comprising a polypeptide according to the invention and a pharmacological excipient and/or carrier.

For a review of gene therapy procedures, see Anderson, Science (1992) 256:808–813; Nabel and Felgner (1993) TIBTECH 11: 211–217; Mitani and Caskey (1993) TIBTECH 11: 162–166; Mulligan (1993) Science 926–932;

Dillon (1993) TIBTECH 11: 167–175; Miller (1992) Nature 357: 455–460; Van Brunt (1988) Biotechnology 6(10): 1149–1154; Vigne (1995) Restorative Neurology and Neuroscience 8: 35–36; Kremer and Perricaudet (1995) British Medical Bulletin 51(1) 31–44; Haddada et al. (1995) in Current Topics in Microbiology and Immunology Doerfler and B÷hm (eds) Springer-Verlag, Heidelberg Germany; and Yu et al., Gene Therapy(1994) 1:13–26.

In yet a further aspect of the present invention there is provided a method of treating diseases and processes that are mediated by endothelial cell proliferation, especially angiogenesis. One such disease which may be treated is cancer.

Thus, this aspect of the invention particularly includes a method of treating a patient in need of anti-angiogenic therapy comprising administering to that patient a vector or host cell comprising nucleic acid sequence encoding a recombinant protein of the present invention.

In accordance with the present invention, it is envisaged that the methods defined herein may be used for treating diseases and processes that are mediated by angiogenesis including, but not limited to, hemangioma, solid tumors, leukemia, metastasis, telangiectasia, psoriasis, scleroderma, pyogenic granuloma, myocardial angiogenesis, plaque neovascularization, coronary collaterals, cerebral collaterals, arteriovenous malformations, ischemic limb angiogenesis, corneal diseases, rubeosis, neovascular glaucoma, diabetic retinopathy, retrolental fibroplasia, arthritis, diabetic neovascularization, macular degeneration, wound healing, peptic ulcer, Helicobacter related diseases, fractures, keloids, vasculogenesis, hematopoiesis, ovulation, menstruation, placentation, and cat scratch fever.

Preferably, the present invention provides a composition for treating or repressing the growth of a cancer. As mentioned above, the recombinant proteins of invention may comprises additional molecules such as peptides or antibodies for targeted delivery of inhibitor-related compositions to specific locations.

Yet another aspect of the invention provides compositions and methods useful for gene therapy for the modulation of endothelial cell proliferation, such as angiogenic processes.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE DRAWINGS

FIG. 1 shows the nucleic acid (SEQ ID NO: 1) and amino acid sequence (SEQ ID NO: 2) of human plasminogen.

FIG. 2 shows the amino acid sequence of human plasminogen (SEQ ID NO: 2).

FIG. 5 shows a representation of human K1–5 of plasminogen with its amino acid sequence shown below (SEQ ID NO: 4).

DETAILED DESCRIPTION OF THE INVENTION

Figure 3:
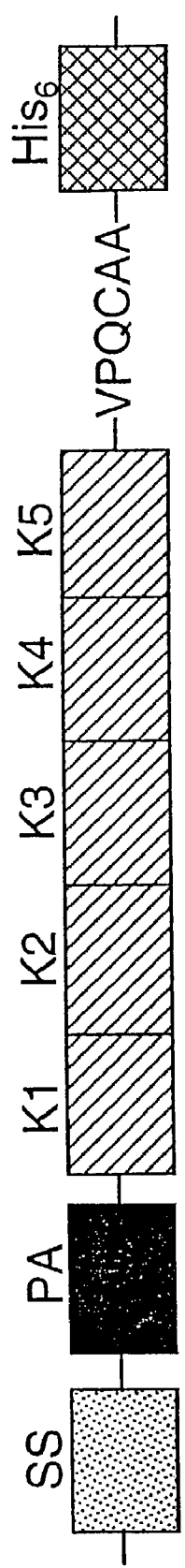
FIG. 3 shows a representation of the structure of angioquiescin. The SS region represents the secretory signal region and the PA region represents the pre-activation region. A peptide tag to help with purification is also identified (SEQ ID NO: 3).
Figure 4:
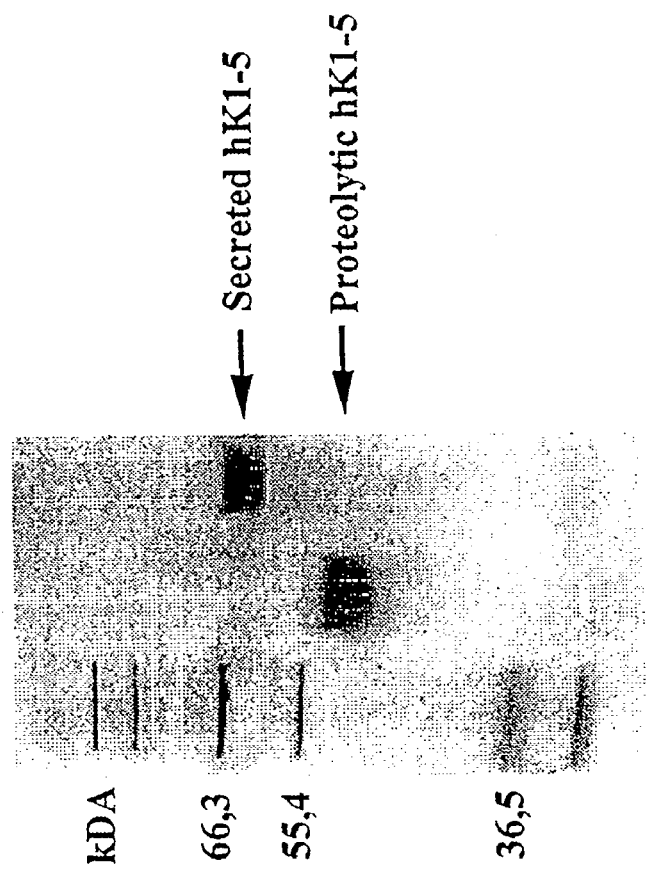
FIG. 4 is a gel image illustrating the difference in molecular weight between the proteolyic human K1–5 and angioquiescin (secreted hK1–5).

In accordance with the present invention, compositions and methods are provided that are effective for inhibiting endothelial cell proliferation, modulating angiogenesis, and inhibiting unwanted angiogenesis, especially angiogenesis related to tumor growth.

It is to be understood that the number of amino acids in the active recombinant molecule may vary and that all closely homologous amino acid sequences that have endothelial inhibiting activity and are capable of being secreted (exported) from cells, i.e. are folded correctly, are contemplated as being included in the present invention.

The present invention particularly provides methods and compositions for treating diseases and processes mediated by undesired and uncontrolled epithelial cell proliferation, such as angiogenesis, by administering to a human or animal having undesired endothelial cell proliferation a composition comprising angioquiescin of human plasminogen capable of inhibiting endothelial cell proliferation in in vitro assays. The term "endothelial inhibiting activity" as used herein means the capability of a molecule to inhibit angiogenesis in general and, for example, to inhibit the growth of bovine capillary endothelial cells in culture in the presence of fibroblast growth factor. This methodology is described below and demonstrated in FIGS. 9, 10 and 11.

Desirably, the isolated protein is at least approximately 80% pure, more desirably at least approximately 90% pure and even more desirable at least approximately 95% pure. The present invention is particularly useful for treating, or for repressing the growth of, tumors. Administration of the inhibitor to a human or animal with prevascularized metastasized tumors helps prevent the growth or expansion of those tumors.

As discussed above, the present invention also encompasses DNA sequences encoding angioquiescin, expression vectors containing DNA sequences encoding angioquiescin eg such as viral vectors, and cells containing one or more expression vectors containing DNA sequences encoding angioquiescin.

The present invention further encompasses gene therapy methods whereby DNA sequences encoding angioquiescin are introduced into a patient to modify in vivo inhibitor levels.

The angioquiescin may be combined with pharmaceutically acceptable excipients, and optionally sustained-release compounds or compositions, such as biodegradable polymers and matrices, to form therapeutic compositions.

The present invention also encompasses a composition comprising a vector containing a DNA sequence encoding angioquiescin, wherein the vector is capable of expressing the recombinant protein when present in a cell, a composition comprising a cell containing a vector, wherein the vector contains a DNA sequence encoding the recombinant protein, and wherein the vector is capable of expressing the protein when present in the cell, and a method comprising implanting into a human or non-human animal a cell containing a vector, wherein the vector contains a DNA sequence encoding angioquiescin, wherein the vector is capable of expressing the protein when present in the cell.

The present invention also encompasses gene therapy, whereby the gene encoding angioquiescin or functional fragment thereof is regulated in a patient. Various methods of transferring or delivering DNA to cells for expression of the gene product protein, otherwise referred to as gene therapy, are disclosed in Gene Transfer into Mammalian Somatic Cells in vivo, N. Yang, Crit. Rev. Biotechn.12 (4): 335–356 (1992), which is hereby incorporated by reference. Gene therapy encompasses incorporation of DNA sequences into somatic cells or germ line cells for use in either ex vivo or in vivo therapy. Gene therapy functions to replace genes, augment normal or abnormal gene function, and to combat infectious diseases and other pathologies.

Strategies for treating these medical problems with gene therapy include therapeutic strategies, such as identifying the defective gene and then adding a functional gene to either replace the function of the defective gene or to augment a slightly functional gene; or prophylactic strategies, such as adding a gene to the product protein that will treat the condition or that will make the tissue or organ more susceptible to a treatment regimen. As an example of a prophylactic strategy, a nucleic acid sequence coding for the inhibitor may be placed in a patient and thus prevent occurrence of angiognesis; or a gene that makes tumor cells more susceptible to radiation could be inserted and then radiation of the tumor would cause increased killing of the tumor cells.

Many protocols for transfer of angioquiescin encoding DNA sequences are envisioned in this invention. Transfection of promoter sequences, other than one normally found specifically associated with the protein, or other sequences which would increase production of the recombinant protein are also envisioned as methods of gene therapy. An example of this technology is found in Transkaryotic Therapies, Inc., of Cambridge, Mass., using homologous recombination to insert a "genetic switch" that turns on an erytropoietin gene in cells. See Genetic Engineering News, Apr. 15, 1994. Such "genetic switches" could be used to activate the recombinant protein in cells not normally expressing the recombinant secretable protein.

Gene transfer methods for gene therapy fall into three broad categories—physical (i.e. electroporation, direct gene transfer and particle bombardment), chemical (lipid-based carriers, or other non-viral vectors) and biological (virus-derived vector and receptor uptake). For example, non-viral vectors may be used which include liposomes coated with DNA. Such liposome/DNA complexes may be directly injected intravenously into the patient. It is believed that the liposome/DNA complexes are concentrated in the liver where they deliver the DNA to macrophages and Kupfter cells. These cells are long lived and thus provide long term expression of the delivered DNA. Additionally, vectors or the "naked" DNA of the gene may be directly injected into the desired organ, tissue or tumor for targeted delivery of the therapeutic DNA.

Gene therapy methodologies can also be described by delivery site. Fundamental ways to deliver genes include ex vivo gene transfer, in vivo gene transfer and in vitro gene transfer. In ex vivo gene transfer, cells are taken from the patient and grown in cell culture. The DNA is transfected into the cells, the transfected cells are expanded in number and then reimplanted in the patient. In in vitro gene transfer, the transformed cells are cells growing in culture, such as tissue culture cells, and not particular cells from a particular patient. These "laboratory cells" are transfected, the transfected cells are selected and expanded for either implantation into a patient or for other uses.

In vivo gene transfer involves introducing the DNA into the cells of the patient when the cells are within the patient. Methods include using a non-infectous virus to deliver the gene in the patient or injecting naked DNA into a site in the patient and the DNA is taken up by a percentage of cells in which the gene product protein is expressed. Additionally, the other methods described herein, such as use of a "gene gun", may be used for in vitro insertion of angioquiescin nucleic acid (DNA or RNA) or functional fragments thereof.

Chemical methods of gene therapy may involve a lipid based compound, not necessarily a liposome, to ferry the DNA across the cell membrane. Lipofectins or cytofectins, lipid-based positive ions that bind to negatively charged DNA, make a complex that can cross the cell membrane and provide the DNA into the interior of the cell. Another chemical method uses receptor-based endocytosis, which involves binding a specific ligand to a cell surface receptor and developing and transporting it across the cell membrane. The ligand binds to the DNA and the whole complex is transported into the cell. The ligand gene complex is injected into the blood stream and then target cells that have the receptor will specifically bind the ligand and transport the ligand-DNA complex into the cell.

Many gene therapy methodologies employ viral vectors to insert genes into cells. For example, altered retrovirus vectors have been used in ex vivo methods to introduce genes into peripheral and tumor-infiltrating lymphocytes, hepatocytes, epidermal cells, myocytes, or other somatic cells. These altered cells are then introduced into the patient to provide the gene product from the inserted DNA. Viral vectors have also been used to insert genes into cells using in vivo protocols. To direct tissue-specific expression of foreign genes, cis-acting regulatory elements or promoters that are known to be tissue specific can be used. Alternatively, this can be achieved using in situ delivery of DNA or viral vectors to specific anatomical sites in vivo. For example, gene transfer to blood vessels in vivo was achieved by implanting in vitro transduced endothelial cells in chosen sites on arterial walls. The virus infected surrounding cells which also expressed the gene product. A viral vector can be delivered directly to the in vivo site, by a catheter for example, thus allowing only certain areas to be infected by the virus, and providing long-term, site specific gene expression. In vivo gene transfer using retrovirus vectors has also been demonstrated in mammary tissue and hepatic tissue by injection of the altered virus into blood vessels leading to the organs.

Viral vectors that have been used for gene therapy protocols include but are not limited to, retroviruses, other RNA viruses such as polio virus or Sindbis virus, adenovirus, adeno-associated virus, herpes viruses, SV 40, vaccinia and other DNA viruses. Replication-defective murine retroviral vectors are the most widely utilized gene transfer vectors. Murine leukemia retroviruses are composed of a single strand RNA complexed with a nuclear core protein and polymerase (pol) enzymes, encased by a protein core (gag) and surrounded by a glycoprotein envelope (env) that determines host range. The genomic structure of retroviruses include the gag, pol and env genes enclosed at by the 5' and 3' long terminal repeats (LTR). Retroviral vector systems exploit the fact that a minimal vector containing the 5' and 3' LTRs and the packaging signal are sufficient to allow vector packaging, infection, and integration into target cells providing that the viral structural proteins are supplied in trans in the packaging cell line. Fundamental advantages of retroviral vectors for gene transfer include efficient infection and gene expression in most cell types, precise single copy vector into target cell chromosomal DNA, and ease of manipulation of the retroviral genome.

The adenovirus is composed of linear double stranded DNA complexed with core proteins and surrounded with capsid proteins. Advances in molecular virology have led to the ability to exploit the biology of these organisms in order to create vectors capable of transducing novel genetic sequences into target cells in vivo. Adenoviral-based vectors will express gene product peptides at high levels. Adenoviral vectors have high efficiencies of infectivity, even with low titers of virus. Additionally, the virus is fully infective as a cell free virion so injection of producer cell lines are not necessary. Another potential advantage to adenoviral vectors is the ability to achieve long term expression of heterologous genes in vivo.

Mechanical methods of DNA delivery include fusogenic lipid vesicles such as liposomes or other vesicles for membrane fusion, lipid particles of DNA incorporating cationic lipid such as lipofectin, polylysine-mediated transfer of DNA, direct injection of DNA, such as microinjection of DNA into germ or somatic cells, pneumatically delivered DNA-coated particles, such as the gold particles used in a "gene gun", and inorganic chemical approaches such as calcium phosphate transfection. Another method, ligand mediated gene therapy, involves complexing the DNA with specific ligands to form ligand-DNA conjugates to direct the DNA to specific cells or tissue.

It has been found that injecting plasmid DNA into muscle cells yields high percentage of the cells which are transfected and have sustained expression of marker genes. The DNA of the plasmid may or may not integrate into the genome ot the cells. Non-integration of the transfected DNA would allow the transfection and expression of gene product proteins in terminally differentiated, non-proliferative tissues for a prolonged period of time without fear of mutational insertions, deletions, or alterations in the cellular or mitochondrial genome. Long-term, but not necessarily permanent transfer of therapeutic genes into specific cells may provide treatments for genetic diseases or for prophylactic use. The DNA could be reinjected periodically to maintain the gene product level without mutations occurring in the genomes of the recipient cells. Non-integration of exogenous DNAs may allow for the presence of several different exogenous DNA constructs within one cell with all of the constructs expressing various gene products.

Particle-mediated gene transfer methods were first used in transforming plant tissue. With a particle bombardment device, or "gene gun", a motive force is generated to accelerate DNA-coated high density particles (such as gold or tungsten) to a high velocity that allows penetration of the target organs, tissues or cells. Particle bombardment can be used in in vitro systems, or with ex vivo or in vivo techniques to introduce DNA into cells, tissues or organs.

Electroporation for gene transfer uses an electrical current to make cells or tissues susceptible to electroporation-mediated gene transfer. A brief electric impulse with a given field strength is used to increase the permeability of a membrane in such a way that DNA molecules can penetrate into the cells. This technique can be used in in vitro systems, or with ex vivo or in vivo techniques to introduce DNA into cells, tissues or organs.

Carrier mediated gene transfer in vivo can be used to transfect foreign DNA into cells. The carrier-DNA-complex can be conveniently introduced into body fluids or the bloodstream and then site specifically directed to the target organ or tissue in the body. Both liposomes and polycations, such as polylysine, lipofectins or cytofectins can be used. Liposomes can be developed which are cell specific or organ specific and thus the foreign DNA carried by the liposome will be taken up by target cells. Injection of immunoliposomes that are targeted to a specific receptor on certain cells can be used as a convenient method of inserting the DNA into the cells bearing the receptor. Another carrier system that has been used is the asialoglycoprotein/polylysine conjugate system for carrying DNA to hepatocytes for in vivo gene transfer.

The transfected DNA may also be complexed with other kinds of carriers so that the DNA is carried to the recipient cell and then resides in the cytoplasm or in the nucleoplasm. DNA can be coupled to carrier nuclear proteins in specifically engineered vesicle complexes and carried directly into the nucleus.

Cells transfected with a DNA sequence encoding angioquiescin may be administered to a patient to provide an in vivo source of inhibitor. For example, cells may be transfected with a vector containing a nucleic acid sequence encoding the recombinant protein.

The term "vector" as used herein means a carrier that can contain or associate with specific nucleic acid sequences, which functions to transport the specific nucleic acid sequences into a cell. Examples of vectors include plasmids and infective microorganisms such as viruses, or non-viral vectors such as ligand-DNA conjugates, liposomes, lipid-DNA complexes. It may be desirable that a recombinant DNA molecule comprising, or consisting of a sequence encoding angioquiescin is operatively linked to an expression control sequence to form an expression vector capable of expressing angioquiescin. The transfected cells may be cells derived from the patient's normal tissue, the patient's diseased tissue, or may be non-patient cells.

For example, tumor cells removed from a patient can be transfected with a vector capable of expressing the secretable angioquiescin protein of the present invention and re-introduced into the patient. The transfected tumor cells produce levels of angioquiescin in the patient that inhibit the growth of the tumor. Patients may be human or non-human animals. Additionally, DNA encoding the angioquiescin may be directly injected, without the aid of a carrier, into a patient. In particular, DNA may be injected into skin, muscle or blood.

Recombinant angioquiescin expression may continue for a long-period of time or nucleic acid encoding the protein may be administered periodically to maintain a desired level of angioquiescin in the cell, the tissue or organ or biological fluid. Although not wanting to be bound by the following hypothesis, it is believed that when a tumor becomes angiogenic it releases one or more angiogenic peptides (e.g. aFGF, bFGF, VEGF, IL-8, GM-CSF, etc.), which act locally, target endothelium in the neighborhood of a primary tumor from an extravascular direction, and do not circulate (or circulate with a short half-life). These angiogenic peptides must be produced in an amount sufficient to overcome the action of endothelial cell inhibitor (inhibitors of angiogenesis) for a primary tumor to continue to expand its population. Once such a primary tumor is growing well, it continues to release endothelial cell inhibitors into the circulation. According to this hypothesis, these inhibitors act remotely at a distance from the primary tumor, target capillary endothelium of a metastasis from an intravascular direction, and continue to circulate. Thus, just at the time when a remote metastasis might begin to initiate angiogenesis, the capillary endothelium in its neighbourhood could be inhibited by incoming inhibitor, e.g. angioquiescin.

Figure 6:
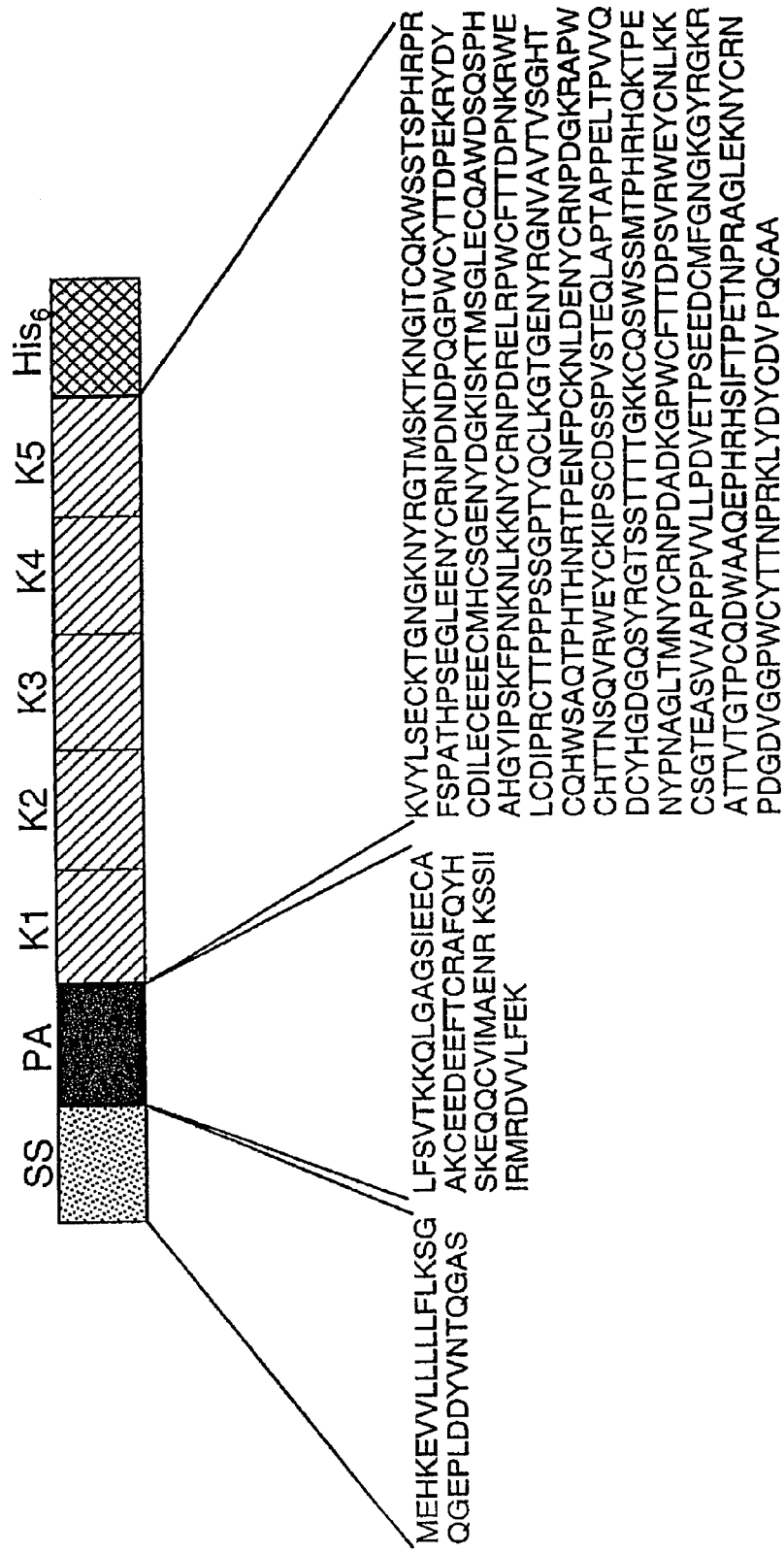
FIG. 6 shows a representation of the structure of angioquiescin along with its amino acid sequence (SEQ ID NO: 5)
Figure 7:
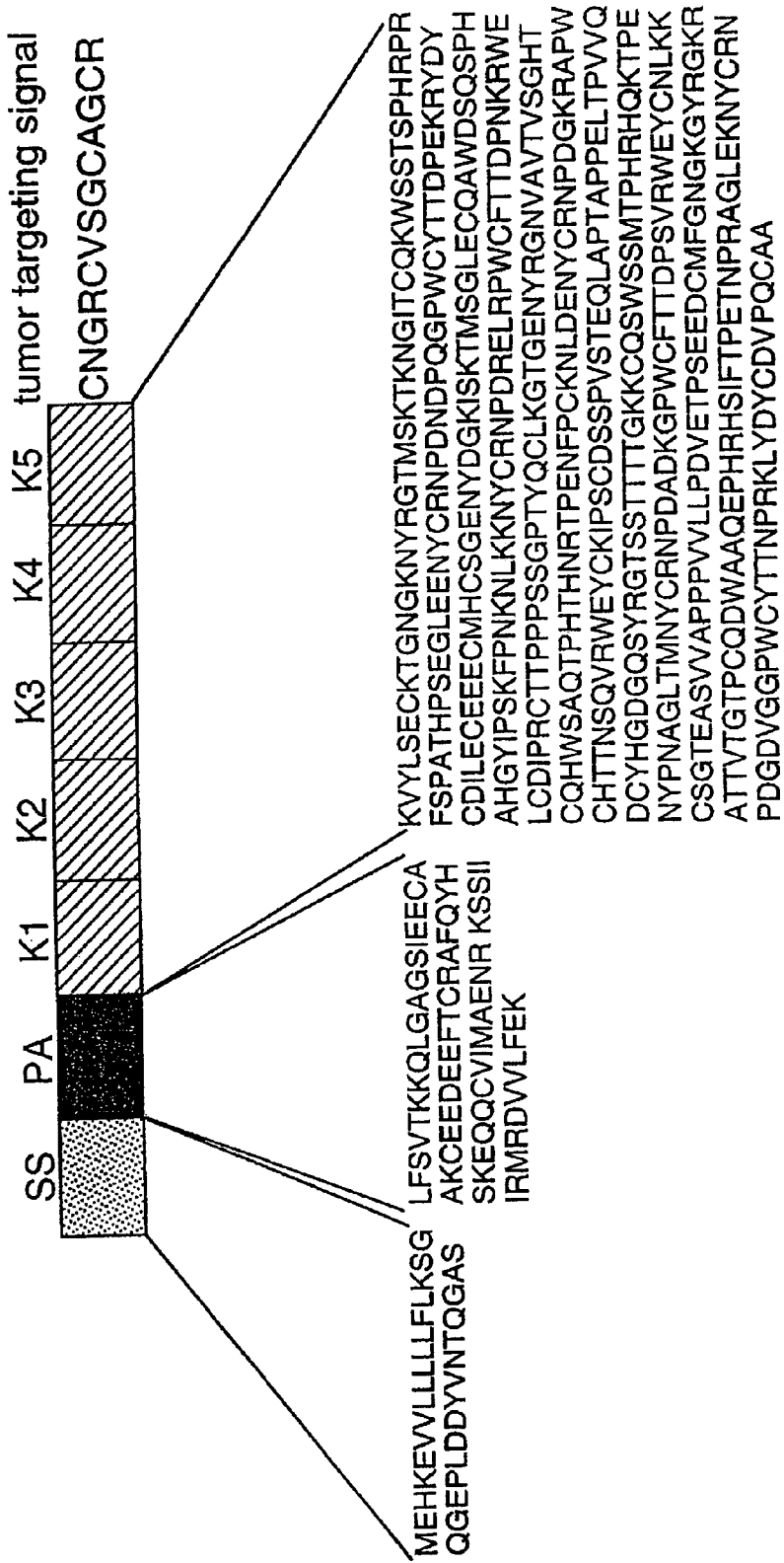
FIG. 7 (SEQ ID NO: 6) shows the representation of FIG. 6 (SEQ ID NO: 5) with an additional tumour targeting signal peptide (SEQ ID NO: 7). This construct was called NGR-signal (see FIG. 10)
Figure 8:
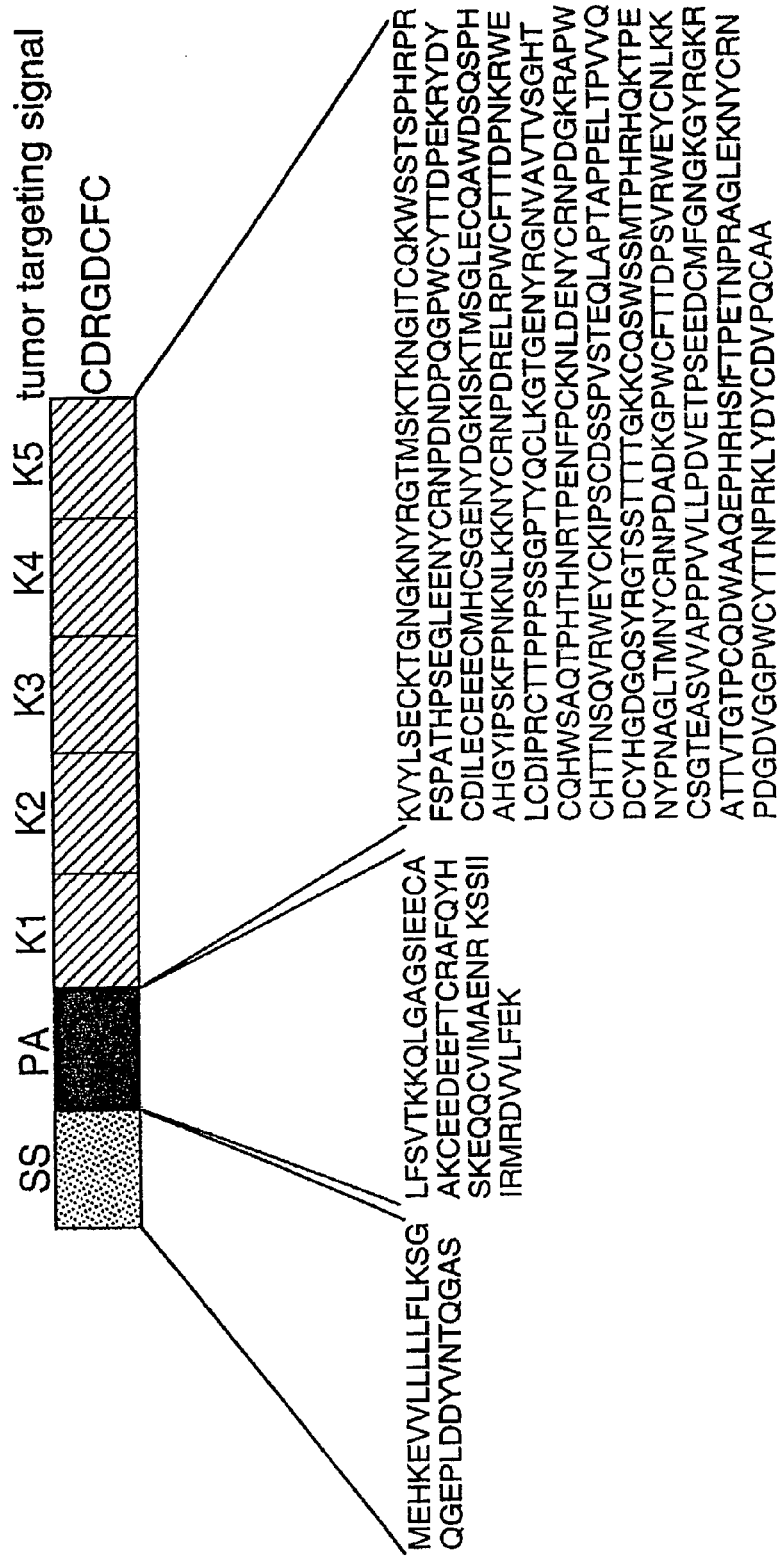
FIG. 8 (SEQ ID NO: 8) show the representation of FIG. 6 (SEQ ID NO: 5) with an additional tumour targeting signal peptide (SEQ ID NO: 9). This construct was called RGD-signal (see FIG. 11)

Production of angioquiescin of the present invention may be accomplished using recombinant DNA techniques including the steps of (1) identifying nucleic acid encoding K1–5 of plasminogen (see FIG. 5 (SEQ ID NO: 4)); (2) identifying the nucleic acid sequence encoding the secretory signal peptide and the pre-activation peptide (see FIG. 6 (SEQ ID NO: 5)); (3) ligating said nucleic acid sequences in a vector expression sequence so as to create an expressable nucleic acid sequence encoding SS/PA/K1–5; (4) inserting the nucleic acid containing vector into a microorganism or other expression system capable of expressing the full sequence, and (5) isolating the recombinantly produced angioquiescin. Appropriate vectors include viral, bacterial and eukaryotic (such as yeast) expression vectors. The above techniques are more fully described in laboratory manuals such as "Molecular Cloning: A Laboratory Manual" Second Edition by Sambrook et al., Cold Spring Harbor Press, 1989, which is incorporated herein by reference. The contents of all references cited in this application are included herein by reference.

Yet another method of producing angioquiescin is by peptide synthesis. The amino acid sequence of the secretable recombinant protein can be determined, for example by automated peptide sequencing methods.

The angioquiescin inhibitor is effective in treating diseases or processes such as angiogenesis, that are mediated by, or involve, endothelial cell proliferation. The present invention includes the method of treating an angiogenesis mediated disease with an effective amount of inhibitor, or a biologically active fragment thereof, or combinations of inhibitor fragments that collectively possess anti-angiogenic activity or inhibitor agonists and antagonists. The angiogenesis mediated diseases include, but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation.

Angioquiescin is useful in the treatment of diseases of excessive or abnormal stimulation of endothelial cells. These diseases include, but are not limited to, intestinal adhesions, atherosclerosis, scleroderma, and hypertrophic scars, i.e., keloids. The protein, or nucleic acid encoding it may be used as a birth control agent by preventing vascularization required for embryo implantation. Angioquiescin may also be useful in the treatment of diseases that have angiogenesis as a pathologic consequenee such as cat scratch disease (Rochele minalia quintosa) and ulcers (Helicobacter pylori).

In addition, labeling angioquiescin or peptide fragments thereof with short lived isotopes enables visualization of receptor binding sites in vivo using positron emission tomography or other modern radiographic techniques in order to locate tumors with inhibitor binding sites.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art.

Material and Methods:

Baculovirus and Insect Cells:

pBlueBac4.5, a baculovirus transfer vector (Invitogen, The Netherlands) containing K1–5 cDNA was propagated in sf9 at 27° C., grown in SF-900 II medium (Gibco, Sweden), supplemented with 10% fetal calf serum. Procedures for maintenance of baculovirus and growth of insect cells followed manufacturer's instructions.

Construction of K1–5 Baculovirus Transfer Vector:

DNA encoding the human plasminogen amino acids 1–562 followed by his-taq at C-terminus was synthetized by a standard polymerase chain reaction (PCR). The K1–5 DNA was ligated into pUC57/T vector (Tamro, Sweden). The K1–5 fragment was cuttout with BamHI and Hind III restriction enzymes to ligate with pBlueBac4.5 baculovirus transfer vector. The sequence was vertiied by sequencing on a ABI model 310 (PE biosystems).

Generation of Recombinant Baculovirus by Co-Transfection:

The K1–5 baculovirus transfer vector was co-transfected with viral DNA (BAC-N-BLUE™ baculovirus expression system linearized DNA, invitrogen, The Netherlands) into sf9 cells according to manufacturer's protocol. Briefly, $2 \times 10^6$ sf9 cells were seeded onto a 60 mm dish. After the cells were firmly attached, on ml of transfection mixture (SF-900 II medium without FCS and INSECTINPLUS™ liposomes, Invitrogen, The Netherlands) containing 4 μg recombinant transfer plasmid and 0.5 μg of viral DNA was added in dropwise into the 60 mm dish. The cells were incubated at room temperature for four hours on a side-to-side rocking platform and one ml of complete SF-900 II medium was added into the dish. After four days incubation at 27° C. the transfection supernatant was harvested. Recombinant viruses were screened with lacZ plaque assay and then with PCR analysis according to manufacturer's protocol. Supernatant with a high virus titer was stored sterile at 4° C.

Production of Angioquiescin

Sf9 cells on T75 flask with approximately 50% confluency was infected with high titer stock virus. The culture supernatant was harvested at three days post-infection by centrifugation. The supernatant was applied to a lysine-SEPHAROSE™ ion exchange column media (Pharmacia, Uppsala, Sweden) column pre-equilibrated with 100 mM Tris-buffer PH 8.0. The column was washed with equilibration buffer and eluted with 200 mM 6-Amino-capronicacid. The sample was dialyzed against water, dried and dissolved in $dH_2O$.

SDS-PAGE Analysis of Recombinant Proteins

Approximately 1 μg of angioquiescin was mixed with SDS sample buffer containing 400 mM Tris-HCI (pH 8) 45% sucrose, 0.1% bromophenol blue, 5% SDS and 20 mM DTT. Boiled sample was analyzed on 4–12% Bis-Tris gel (Novex) and stained with Coomassie stain (45% methanol, 9% glacial acetic acid, and 1.25% (v/v) coomassie blue). Human proteolytic K1–5 was used as control.

Figure 9:
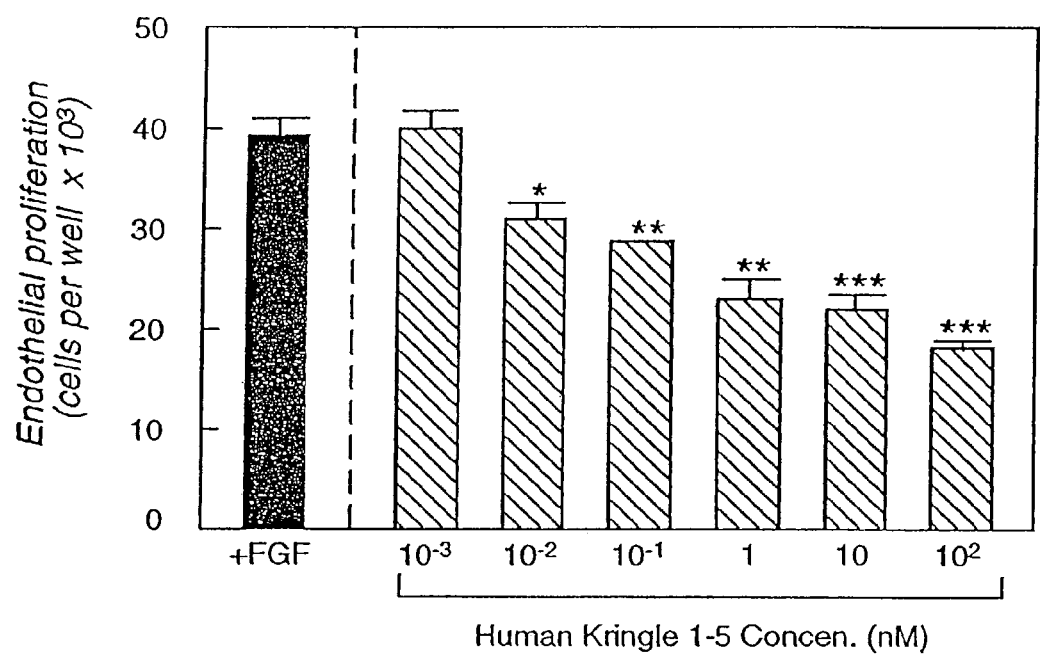
FIG. 9 shows inhibition of endothelial cell proliferation. Purified angioquiescin (recombinant human K1–5) at various concentrations was assayed on BCE cells in the presence of 1 ng/ml of FGF-2 in a 72-h proliferation experiment as described in the Materials and Methods. Angioquiescin displays a dose-dependent effect on suppression of BCE cell growth. Values represent the mean (±SEM) of triplicate of each sample.
Figure 10:
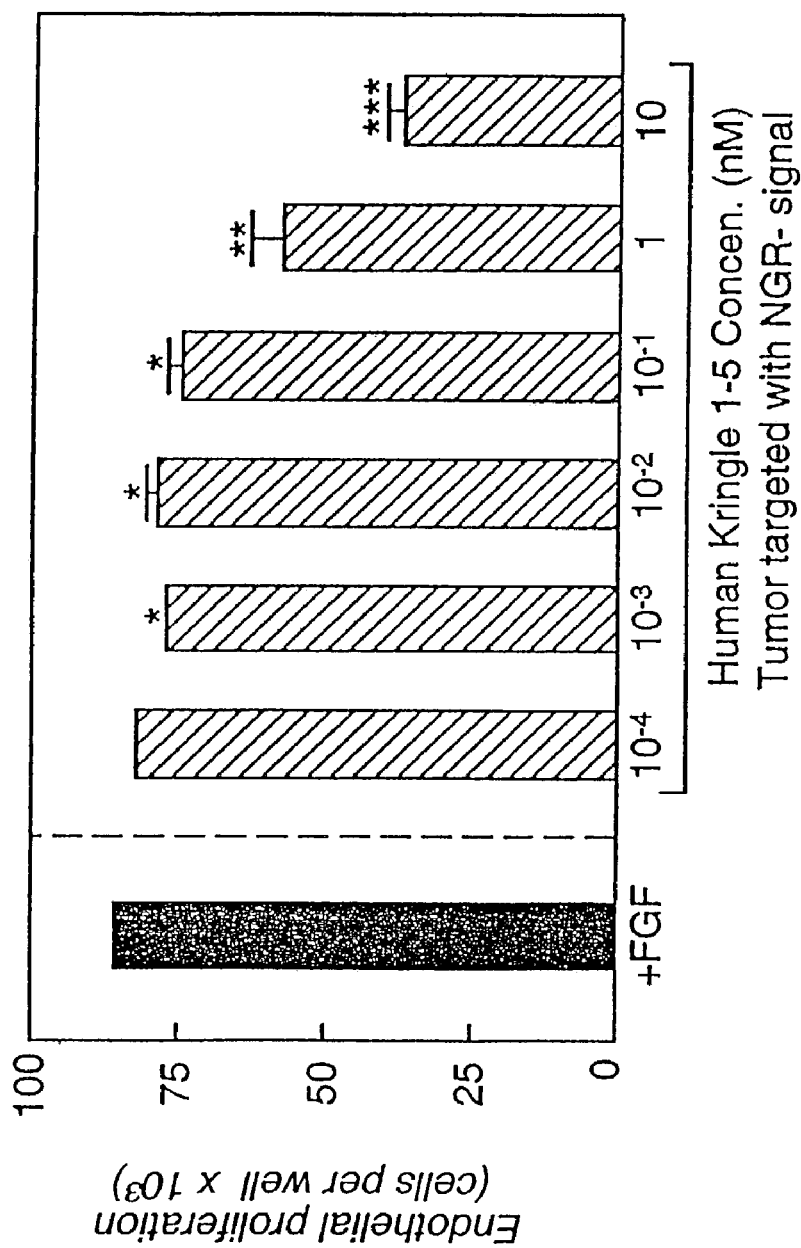
FIG. 10 shows inhibition of endothelial cell proliferation. Purified angioquiescin (human Kringle 1–5) with a NGR-based tumor targeting peptide at various concentrations was assayed on BCE cells in the presence of 1 ng/ml of FGF-2 in a 72-h proliferation experiment as described in the Materials and Methods. Angioquiescin displays a dose-dependent effect on suppression of BCE cell growth. Values represent the mean (±SEM) of triplicate of each sample.
Figure 11:
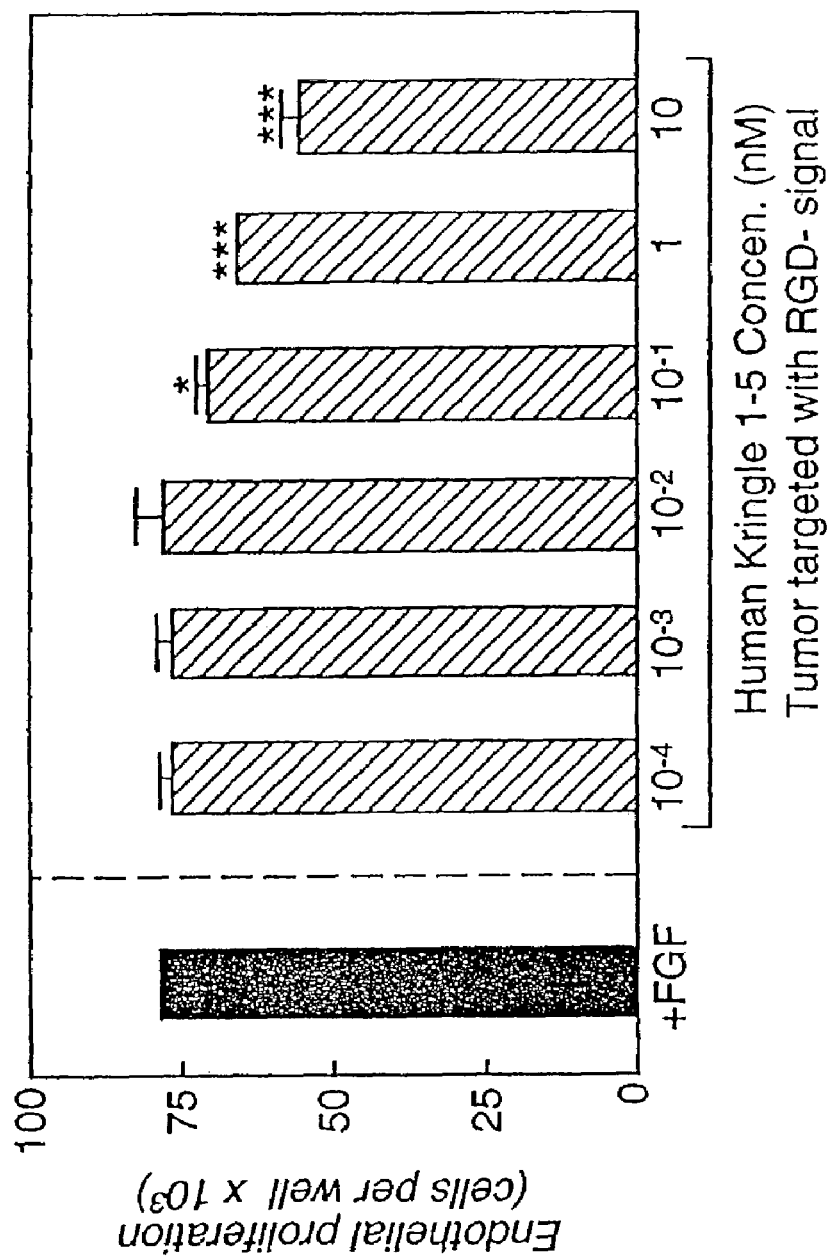
FIG. 11 inhibition of endothelial cell proliferation. Purified angioquiescin with a RGD-based tumor targeting peptide at various concentrations was assayed on BCE cells in the presence of 1 ng/ml of FGF-2 in a 72-h proliferation experiment as described in the Materials and Methods. K1–5 displays a dose-dependent effect on suppression of BCE cell growth. Values represent the mean (±SEM) of triplicate of each sample.

Endothelial Cell Proliferation Assay (FIGS. 9 to 11)

Bovine capillary endothelial cells were maintained in DME medium containing 10% BCS and 3 ng/ml of recombinant human FGF-2. Cells growing in gelatinized 6 well plates were trypsinized and resuspended in DME medium containing 5% BCS. Approximately 10,000 cells in 0.5 ml medium were added to each gelatinized well of 24 well plates and incubated at 37° C. in 10% $CO_2$ for one hour. After one hour incubation, different concentrations of K1–5 were added to each well in triplicates. After another hour of incubation, FGF-2 was added to a final concentration of 1 ng/ml. After 72 hr, cells were trypsinized, resuspended in Isoton II solution (Coulter Electronics Ltd. Beds, England) and counted with a Coulter counter.

Bovine capillary endothelial (BCE) cells were isolated as described previously (Folkman, J., Haudenschild, C. C. & Zetter, B. R. (1979) *Proc. Natl. Acad. Sci. USA.* 76, 5217–5121.). BCE cells were maintained in DME medium containing 10% heat-inactivated bovine calf serum (BCS) and 3 ng/ml of recombinant human bFGF. Cells growing in gelatinized 6-well plates were dispersed in 0.05% solution and resuspended with DME medium containing 10% BCS. Approximately 10,000 cells in 0.5 ml were added to each gelatinized wells of 24-well plates and incubated at 37° C. for 24 h. The medium was replaced with 0.5 ml fresh DME medium containing 5% BCS and samples of kringle structures in triplicates were added to each well. After 30 min incubation, bFGF was added to a final concentration of 1 ng/ml. After 72 h incubation, cells were trypsinized, resuspended in Isoton II solution (Coulter Electronics Ltd. Beds, England) and counted with Coulter counter.

What is claimed is:

1. A pharmaceutical composition comprising a recombinant protein having the amino acid sequence of Kringle 1 to 5, a secretory signal peptide and a pre-activation peptide, which are the Kringle 1 to 5, secretory signal peptide and pre-activation peptide of a mammalian plasminogen, wherein said protein has anti-angiogenic activity, and wherein the amino acid sequence of Kringle 1 to 5 consists of the sequence of amino acids 97–562 of SEQ ID NO: 5.

2. A pharmaceutical composition comprising a recombinant protein consisting essentially of having the amino acid sequence of that of Kringle 1 to 5, a secretory signal peptide and a pre-activation peptide, which are the Kringle 1 to 5, secretory signal peptide and pre-activation peptide of a mammalian plasminogen, wherein said protein has anti-angiogenic activity, and wherein the amino acid sequence of Kringle 1 to 5 consists of the sequence of amino acids 97–562 of SEQ ID NO: 5.

3. A pharmaceutical composition according to claim 1 wherein the recombinant protein has a molecular weight of between 55 kD and 69 kD.

4. A pharmaceutical composition according to claim 3 wherein the recombinant protein has a molecular weight of about 65 kD.

5. A pharmaceutical composition according to claim 1 wherein the recombinant protein further comprises a tumour targeting peptide.

6. A pharmaceutical composition according to claim 5 wherein said tumour targeting peptide comprises an amino acid sequence selected from the group consisting of CNGRCVSCCAGCR (SEQ ID NO. 7) and CDRGDCFC (SEQ ID NO. 9).

7. A pharmaceutical composition according to claim 1 further comprising a pharmaceutically acceptable carrier.

8. A recombinant protein comprising having the amino acid sequence of Kringle 1–5, a secretory signal peptide and a preactivation peptide, which are the Kringle 1 to 5, secretory signal peptide and pre-activation peptide of a mammalian plasminogen, wherein the amino acid sequence of Kringle 1 to 5 consists of the sequence of amino acids 97–562 of SEQ ID NO: 5, and wherein the preactivation peptide comprises the sequence of amino acids 33–96 of SEQ ID NO. 5, and wherein the protein has anti-angiogenic activity.

9. A recombinant protein according to claim 8 having a molecular weight of between 55 kD and 69 kD.

10. A recombinant protein according to claim 9 having a molecular weight of about 65 kD.

11. A recombinant protein according to claim 8 further comprising a tumour targeting peptide.

12. A recombinant protein according to claim 11 wherein said tumour targeting peptide comprises an amino acid sequence selected from the group consisting of CNGRCVSCCAGCR (SEQ ID NO. 7) and CDRGDCFC (SEQ ID NO. 9).

13. A method of treating a patient in need of anti-angiogenic therapy comprising administering to that patient an effective dose of a recombinant protein according to claim 8.

14. A pharmaceutical composition comprising the recombinant protein according to claim 8.

15. A recombinant protein comprising having the amino acid sequence of Kringle 1–5, a secretory signal peptide and a preactivation peptide, which are the Kringle 1 to 5, secretory signal peptide and preactivation peptide of a mammalian plasminogen, wherein the amino acid sequence of Kringle 1 to 5 consists of the sequence of amino acids 97–562 of SEQ ID NO: 5, and wherein the secretory signal peptide comprises the sequence of amino acids 1–32 of SEQ ID NO. 5, and wherein the protein has anti-angiogenic activity.

16. A recombinant protein according to claim 15 having a molecular weight of between 55 kD and 69 kD.

17. A recombinant protein according to claim 16 having a molecular weight of about 65 kD.

18. A recombinant protein according to claim 15 further comprising a tumour targeting peptide.

19. A recombinant protein according to claim 18 wherein said tumour targeting peptide comprises an amino acid sequence selected from the group consisting of CNGRCVSGCAGCR (SEQ ID NO. 7) and CDRGDCFC (SEQ ID NO. 9).

20. A method of treating a patient in need of anti-angiogenic therapy comprising administering to that patient an effective dose of a recombinant protein according to claim 15.

21. A pharmaceutical composition comprising the recombinant protein according to claim 15.

22. A recombinant protein comprising the amino acid sequence of Kringle 1–5, a secretory signal peptide, an a preactivation peptide, which are the Kringle 1 to 5, secretory signal peptide and a preactivation peptide of a mammalian plasminogen, wherein the recombinant protein further comprises a tumour targeting polypeptide and wherein said tumour targeting peptide comprises an amino acid sequence selected from the group consisting of CNGRCVSGCAGCR (SEQ ID NO: 7) and CDRGDCFC (SEQ ID NO: 9).

23. A pharmaceutical composition comprising the recombinant protein according to claim 22.

24. A recombinant protein according to claim 22 having a molecular weight of between 55 kD and 69 kD.

25. A recombinant protein according to claim 24 having a molecular weight of about 65 kD.

* * * * *